(12) United States Patent
Simioni

(10) Patent No.: US 9,982,248 B2
(45) Date of Patent: *May 29, 2018

(54) FACTOR IX POLYPEPTIDE MUTANT, ITS USES AND METHOD FOR ITS PRODUCTION

(71) Applicant: uniQure biopharma B.V., Amsterdam (NL)

(72) Inventor: Paolo Simioni, Padua (IT)

(73) Assignee: UNIQURE BIOPHARMA B.V., Amsterdam (NL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/650,070

(22) Filed: Jul. 14, 2017

(65) Prior Publication Data

US 2017/0355973 A1    Dec. 14, 2017

Related U.S. Application Data

(63) Continuation of application No. 14/981,981, filed on Dec. 29, 2015, which is a continuation of application No. 13/063,898, filed as application No. PCT/EP2009/061935 on Sep. 15, 2009, now Pat. No. 9,249,405.

(30) Foreign Application Priority Data

Sep. 15, 2008  (IT) .............................. BO2008A0564
May 6, 2009    (IT) .............................. BO2009A0275

(51) Int. Cl.
    *C12N 9/64*      (2006.01)
    *A61K 38/48*     (2006.01)

(52) U.S. Cl.
    CPC .......... *C12N 9/644* (2013.01); *A61K 38/4846* (2013.01); *C12Y 304/21022* (2013.01)

(58) Field of Classification Search
    None
    See application file for complete search history.

(56) References Cited

U.S. PATENT DOCUMENTS

| 5,171,569 | A |       | 12/1992 | Anson et al. | |
|---|---|---|---|---|---|
| 5,223,408 | A |       | 6/1993  | Goeddel et al. | |
| 6,227,618 | B1 |      | 5/2001  | Ligon, Sr. et al. | |
| 6,277,618 | B1 |      | 8/2001  | Kopetzki et al. | |
| 6,315,995 | B1 |      | 11/2001 | Pinsky et al. | |
| 6,531,298 | B2 | *    | 3/2003  | Stafford ................. | C12N 9/644 435/226 |
| 7,700,734 | B2 | *    | 4/2010  | Lin ................. | C12Y 304/21022 435/7.1 |
| 7,888,067 | B2 | *    | 2/2011  | Lin ................. | C12Y 304/21022 435/320.1 |
| 8,383,388 | B2 |      | 2/2013  | Oyhenart et al. | |
| 8,778,870 | B2 |      | 7/2014  | Madison et al. | |
| 9,249,405 | B2 |      | 2/2016  | Simioni | |

| 2002/0031799 | A1 | * | 3/2002  | Stafford ................. | C12N 9/644 435/69.1 |
|---|---|---|---|---|---|
| 2002/0166130 | A1 |   | 11/2002 | Velander et al. | |
| 2004/0102388 | A1 |   | 5/2004  | High et al. | |
| 2004/0110675 | A1 |   | 6/2004  | Sheehan | |
| 2004/0110688 | A1 |   | 6/2004  | Bajaj et al. | |
| 2004/0133930 | A1 |   | 6/2004  | Cooper et al. | |
| 2004/0146938 | A1 |   | 6/2004  | Nguyen et al. | |
| 2004/0254106 | A1 |   | 12/2004 | Carr et al. | |
| 2005/0100982 | A1 |   | 5/2005  | DeFrees et al. | |
| 2006/0040856 | A1 |   | 2/2006  | DeFrees et al. | |
| 2006/0188482 | A1 |   | 8/2006  | Kay et al. | |
| 2007/0093443 | A1 |   | 4/2007  | Madison et al. | |
| 2007/0243526 | A1 | * | 10/2007 | Kay ..................... | C07K 14/005 435/5 |
| 2007/0243615 | A1 | * | 10/2007 | Qu .......................... | C12N 7/00 435/456 |
| 2007/0244036 | A1 | * | 10/2007 | Scheiflinger ........... | A61K 38/36 514/14.2 |
| 2007/0274908 | A1 | * | 11/2007 | Pasqualini ....... | A61K 47/48238 424/1.17 |
| 2007/0280906 | A1 | * | 12/2007 | Petras ..................... | C12N 7/00 424/93.2 |
| 2008/0003202 | A1 |   | 1/2008  | Guyon et al. | |
| 2008/0102115 | A1 | * | 5/2008  | Oyhenart ............... | C12N 9/644 424/457 |

(Continued)

FOREIGN PATENT DOCUMENTS

BR    PI0705943-4 A2    12/2008
EP    2 048 236 A1      4/2009

(Continued)

OTHER PUBLICATIONS

Ahmad et al., "The role of the first growth factor domain of human factor IXa in binding to platelets and in factor X activation," J Bio Chem, 267(12):8571-8576, (1992).

Altschul et al., "Basic local alignment search tool," J Mol Biol, 215(3):403-410, (1990).

Altschul et al., "Gapped BLAST and PSI-BLAST: a new generation of protein database search programs," Nucleic Acids Res, 25(17):3389-3402, (1997).

Ameri et al., "Myocardial fibrosis in mice with overexpression of human blood coagulation factor IX," Blood, 101:1871-1873, (2003).

Anson et al., "The gene structure of human anti-haemophilic factor IX," EMBO J, 3(5):1053-1060, (1984).

Betts et al., "Amino Acid Properties and Consequences of Substitutions," Bioinformatics for Geneticists, Chapter 14, Edited by Michael Barnes and Ian Gray, pp. 289-316, (2003).

(Continued)

*Primary Examiner* — Amber D Steele
(74) *Attorney, Agent, or Firm* — Finnegan, Henderson, Farabow, Garrett & Dunner, LLP

(57) ABSTRACT

Disclosed are a modified FIX (factor IX) polypeptide comprising a leucine, cysteine, aspartic acid, glutamic acid, histidine, lysine, asparagine, glutamine or tyrosine in position 338; pharmaceutical preparations containing said modified FIX polypeptide; a nucleotide sequence coding for the modified FIX polypeptide; and a method for producing the modified FIX polypeptide.

20 Claims, No Drawings

(56) References Cited

U.S. PATENT DOCUMENTS

| | | | |
|---|---|---|---|
| 2008/0167219 A1* | 7/2008 | Lin | C12N 9/644 530/384 |
| 2008/0260820 A1 | 10/2008 | Borrelly et al. | |
| 2008/0305991 A1 | 12/2008 | DeFrees et al. | |
| 2012/0164130 A1 | 6/2012 | Brooks et al. | |
| 2015/0283267 A1 | 10/2015 | Vandendriessche et al. | |
| 2016/0304851 A1 | 10/2016 | Schüttrumpf et al. | |
| 2016/0375110 A1 | 12/2016 | High et al. | |

FOREIGN PATENT DOCUMENTS

| | | |
|---|---|---|
| EP | 1 781 782 B2 | 5/2010 |
| EP | 2 368 983 B1 | 8/2016 |
| EP | 2 767 587 B1 | 4/2017 |
| WO | WO 96/00577 | 1/1996 |
| WO | WO 99/03496 | 1/1999 |
| WO | WO 99/49880 | 10/1999 |
| WO | WO 01/70763 A1 | 9/2001 |
| WO | WO 02/40544 A2 | 5/2002 |
| WO | WO 02/096454 A1 | 12/2002 |
| WO | WO 03/020764 A2 | 3/2003 |
| WO | WO 2006/018204 | 2/2006 |
| WO | WO 2006/031226 A1 | 3/2006 |
| WO | WO 2006/048777 | 5/2006 |
| WO | WO 2006/066066 A2 | 6/2006 |
| WO | WO 2007/075976 A2 | 7/2007 |
| WO | WO 2007/089632 A2 | 8/2007 |
| WO | WO 2007/135182 A2 | 11/2007 |
| WO | WO 2007/149406 | 12/2007 |
| WO | WO 2007/149852 A2 | 12/2007 |
| WO | WO 2008/092643 | 8/2008 |
| WO | WO 2008/118507 A2 | 10/2008 |
| WO | WO 2008/119815 A1 | 10/2008 |
| WO | WO 2008/127654 A2 | 10/2008 |
| WO | WO 2009/051717 A2 | 4/2009 |
| WO | WO 2009/130198 A2 | 10/2009 |
| WO | WO 2009/137254 | 11/2009 |
| WO | WO 2009/140015 A2 | 11/2009 |
| WO | WO 2010/012451 A1 | 2/2010 |
| WO | WO 2010/029178 A1 | 3/2010 |
| WO | WO 2010/151736 A1 | 12/2010 |
| WO | WO 2011/014890 A1 | 2/2011 |
| WO | WO 2016/146757 A1 | 9/2016 |
| WO | WO 2017/024060 A1 | 2/2017 |

OTHER PUBLICATIONS

Bond et al., "Biochemical characterization of recombinant factor IX," Semin Hematol, 35(2 Suppl 2):11-7, (1998).

Bowie et al., "Deciphering the message in protein sequences: tolerance to amino acid substitutions," Science, 247(4948):1306-1310, (1990).

Chang et al., "Changing residue 338 in human factor IX from arginine to alanine causes an increase in catalytic activity," J Biol Chem, 273(20):12089-12094, (1998).

Cheung et al., "The binding of human factor IX to endothelial cells is mediated by residues 3-11," J Biol Chem, 267(29):20529-20531, (1992).

Dayoff et al., "A Model of Evolutionary Change in Proteins," Atlas of Protein Seq Struc, 3:345-352, (1978).

Devereux et al., "A comprehensive set of sequence analysis programs for the VAX," Nucleic Acids Res, 12(1 Pt 1):387-395, (1984).

Franchini et al., "Treatment of hemophilia B: focus on recombinant factor IX," Biologics, 7:33-38, (2013).

French et al., "What is a Conservative Substitution?", J Mol Evol, 19:171-175, (1983).

Friedler et al., "Development of a functional backbone cyclic mimetic of the HIV-1 Tat arginine-rich motif," J Biol Chem, 275(31):23783-23789, (2000).

Giannelli et al., "Haemophilia B: database of point mutations and short additions and deletions," Nucleic Acids Res, 18(14):4053-4059, (1990).

Giu et al., "Circulating and binding characteristics of wild-type factor IX and certain Gla domain mutants in vivo," Blood, 100(1):153-158, (2002).

Green, "Hemophilia B Mutational Analysis," Hemostasis and Thrombosis Protocols, Methods in Molecular Medicine, 31:159-167, (1999).

Karlin et al., "Methods for assessing the statistical significance of molecular sequence features by using general scoring schemes," Proc Natl Acad Sci U S A, 87(6): 2264-2268, (1990).

Karlin et al., "Applications and statistics for multiple high-scoring segments in molecular sequences," Proc Natl Acad Sci U S A, 90(12):5873-5877, (1993).

Khalilzadeh et al., "Process development for production of recombinant human interferon-gamma expressed in *Escherichia coli*," J Ind Microbiol Biotechnol, 31(2):63-69, (2004).

Kowarsch et al., "Correlated mutations: a hallmark of phenotypic amino acid substitutions," PLoS Comput Biol, 6(9):e1000923, (2010).

Kunkel, "Rapid and efficient site-specific mutagenesis without phenotypic selection," Proc Natl Acad Sci U S A, 82(2):488-492, (1985).

Kurachi et al., "Isolation and characterization of a cDNA coding for human factor IX," Proc Natl Acad Sci U S A, 79(21):6461-6464, (1982).

Lin et al., "Expression and characterization of human factor IX and factor IX-factor X chimeras in mouse C127 cells," J Biol Chem, 265(1):144-150, (1990).

Lowe, "Factor IX and thrombosis," Br J Haematol, 115(3):507-513, (2001).

Mathur et al., "Protease and EGF1 domains of factor IXa play distinct roles in binding to factor VIIIa. Importance of helix 330 (helix 162 in chymotrypsin) of protease domain of factor IXa in its interaction with factor VIIIa," J Biol Chem, 274(26):18477-18486, (1999).

Mayfield et al., "Expression and assembly of a fully active antibody in algae," Proc Natl Acad Sci U S A, 100(2):438-442, (2003).

Muneta et al., "Large-scale production of porcine mature interleukin-18 (IL-18) in silkworms using a hybrid baculovirus expression system," J Vet Med Sci, 65(2):219-223, (2003).

Murphy et al., "Gene therapy for haemophilia," Br J Haematol, 140(5):479-487, (2008).

Ng et al., "Predicting deleterious amino acid substitutions," Genome Res, 11(5):863-874, (2001).

Ng et al., "Predicting the effects of amino acid substitutions on protein function," Annu Rev Genomics Hum Genet, 7:61-80, (2006).

Palmer et al., "Production of human factor IX in animals by genetically modified skin fibroblasts: potential therapy for hemophilia B," Blood, 73(2):438-445, (1989).

Pham et al., "Large-Scale Transient Transfection of Serum-Free Suspension-Growing HEK293 EBNA1 Cells: Peptode Additives Improve Cell Growth and Transfection Efficiency," Biotechnol Bioeng, 84(3):332-342, (2003).

Platis et al., "High yield expression, refolding, and characterization of recombinant interferon alpha2/alpha8 hybrids in *Escherichia coli*," Protein Expr Purif, 31(2):222-230, (2003).

Sabatino et al., "Novel hemophilia B mouse models exhibiting a range of mutations in the Factor IX gene," Blood, 104(9):2767-2774, (2004).

Schaub et al., "Preclinical studies of recombinant factor IX," Semin Hematol, 35(2 Suppl 2):28-32, (1998).

Schuettrumpf et al., "Factor IX variants improve gene therapy efficacy for hemophilia B," Blood, 105(6):2316-2323, (2005).

Simioni et al., "X-linked thrombophilia with a mutant factor IX (factor IX Padua)," N Engl J Med, 361(17):1671-1675, (2009).

Skoko et al., "Expression and characterization of human interferon-beta1 in the methylotrophic yeast *Pichia pastoris*," Biotechnol Appl Biochem, 38(Pt 3):257-265, (2003).

Toomey et al., "Inhibition of factor IX(a) is protective in a rat model of thromboembolic stroke," Stroke, 33(2):578-585, (2002).

Wajih et al., "Increased production of functional recombinant human clotting factor IX by baby hamster kidney cells engineered

(56) References Cited

OTHER PUBLICATIONS to overexpress VKORC1, the vitamin K 2,3-epoxide-reducing enzyme of the vitamin K cycle," J Biol Chem, 280(36):31603-31607, (2005).
Wang et al., "Predicting Functional Impact of Single Amino Acid Polymorphisms by Integrating Sequence and Structural Features," IEEE International Conference on Systems Biology, pp. 18-26, (2011).
Yampolsky et al., "The exchangeability of amino acids in proteins," Genetics, 170(4):1459-1472, (2005).
Yan et al., "Transgenic mice can express mutant human coagulation factor IX with higher level of clotting activity," Biochem Genet, 44(7-8):349-360, (2006).
Yao et al., "Expression of human factor IX in rat capillary endothelial cells: toward somatic gene therapy for hemophilia B," Proc Natl Acad Sci U S A, 88(18):8101-8105, (1991).
Yoshitake et al., "Nucleotide sequence of the gene for human factor IX (antihemophilic factor B)," Biochemistry, 24(14):3736-3750, (1985).
PCT International Search Report issued for PCT Application No. PCT/EP2009/061935 filed on Sep. 15, 2009 in the name of Paolo Simioni.
PCT Written Opinion issued for PCT Application No. PCT/EP2009/061935 filed on Sep. 15, 2009 in the name of Paolo Simioni.
PCT International Preliminary Report on Patentability issued for PCT Application No. PCT/EP2009/061935 filed on Sep. 15, 2009 in the name of Paolo Simioni.
STN—The Choice of Patent Experts. CAS Registry Fact Sheet, 1 page, (2014).
Bajaj et al., "Factor IXa:factor VIIIa interaction. helix 330-338 of factor ixa interacts with residues 558-565 and spatially adjacent regions of the a2 subunit of factor VIIIa," J Biol Chem, 276(19):16302-16309, (2001).
Bottema et al., "The pattern of spontaneous germ-line mutation: relative rates of mutation at or near CpG dinucleotides in the factor IX gene," Hum Genet, 91(5):496-503, (1993).
Brunetti-Pierri et al., "Bioengineered factor IX molecules with increased catalytic activity improve the therapeutic index of gene therapy vectors for hemophilia B," Hum Gene Ther. 20(5):479-485, (2009).
Chang et al., "Residues 330-338 in Catalytic Domain of Factor IX Represent an Interactive Site for Both Factor VIIIa and Factor X," Blood, Abstract #744, The American Society of Hematology Fortieth Annual Meeting, (1998).
Driscoll et al., "A Codon 338 Nonsense Mutation in the Factor IX Gene in Unrelated Hemophilia B Patients: Factor IX[338 New York]," Blood, 74(2):737-742, (1989).
Finn et al., "FIX-R338L (FIX Padua) as a Successful Alternative for the Treatment of Canine Severe Hemophilia B," Abstract 694, Blood, 114:694, (2009).
Finn et al., "The efficacy and the risk of immunogenicity of FIX Padua (R338L) in hemophilia B dogs treated by AAV muscle gene therapy," Blood, 120(23):4521-4523, (2012).
Goree et al., "Characterization of the mutations causing hemophilia B in 2 domestic cats," J Vet Intern Med, 19(2):200-204,(2005).
Hamaguchi et al., "Expression and Characterization of Human Factor IX," The Journal of Biological Chemistry, 266(23):15213-15220, (1991).
Hamaguchi et al., "Mutations in the catalytic domain of factor IX that are related to the subclass hemophilia Bm," Biochemistry, 32(25):6324-6329, (1993).

Ketterling et al., "The rates of G:C → T:A and G:C → C:G transversions at CpG dinucleotides in the human factors IX gene," Am J Hum Genet, 54(5):831-835, (1994).
Kolkman et al., "Regions 301-303 and 333-339 in the catalytic domain of blood coagulation factor IX are factor VIII-interactive sites involved in stimulation of enzymatic activity," Biochem J, 339 (Pt 2): 217-221, (1999).
Liu et al., "Nonsense Suppression in Approaches in Treating Hemophilia," Blood, Abstract, 112:512, (2008).
Lu et al., "Gene therapy for hemophilia B mediated by recombinant adeno-associated viral vector with hFIXR338A, a high catalytic activity mutation of human coagulation factor IX," Science in China, 44(6):585-592, (2001).
Ludwig et al., "Identification of a single nucleotide C-to-T transition and five different deletions in patients with severe hemophilia B," Am J Hum Genet, 45(1):115-122, (1989).
Rohlena et al., "Residues Phe342-Asn346 of activated coagulation factor IX contribute to the interaction with low density lipoprotein receptor-related protein," J Biol Chem, 278(11):9394-9401, (2003).
Schuettrumpf et al., "The Use of Factor IX Variants Improves AAV-Mediated Gene Therapy for Hemophilia B," Blood, Abstract #52, Program of the 44th Annual Meeting of the American Society of Hematology, (2002).
Simioni et al., "Evidence of the first X-linked thrombophilia gene mutation in clotting factor IX resulting in a hyperfunctional protein (FIX Padua)," PowerPoint Presentation Slides, XXII ISTH Congress, Boston, (2009).
Simioni et al., "Evidence of the first X-linked thrombophilia due to a novel mutation in clotting factor IX gene resulting in hyperfunctional fix: factor IX arginine 338 leucine (factor IX padua)," Oral Presentations, PL-TU-004, International Society on Thrombosis and Haemostasis 7 (Suppl. 2), (2009).
Spitzer et al., "Molecular defect in factor IXBm Lake Elsinore. Substitution of Ala390 by Val in the catalytic domain," J Blol Chem, 263(22):10545-10548, (1988).
Spitzer et al., "Replacement of isoleucine-397 by threonine in the clotting proteinase factor IXa (Los Angeles and Long Beach variants) affects macromolecular catalysis but not L-tosylarginine methyl ester hydrolysis. Lack of correlation between the ox brain prothrombin time and the mutation site in the variant proteins," Biochem J, 265(1):219-225, (1990).
Tsang et al., "A factor IX mutation, verified by direct genomic sequencing, causes haemophilia B by a novel mechanism," EMBO J, 7(10):3009-3015, (1988).
Ware et al., "Genetic defect responsible for the dysfunctional protein: factor IXLong Beach," Blood, 72(2):820-822,(1988).
Yan, "The current feature of the study on human coagulation factor IX mutant," Yi Chuan, 27(5):833-838, (2005).
Young et al., "Three novel and one C31133T (Arg-338→Stop) mutations of antihemophilic factor IX gene detected in Taiwan," Zhonghua Yi Xue Za Zhi Taipei, 57(4):241-246, (1996).
ISTH 2009 Daily, "Long-acting Factor VIIa had Longer Duration of Action in Hemophilic A Mice," XXII Congress International Society on Thrombosis and Haemostatis, Boston, MA, 2 pages, (2009).
Third Party Observation for European Application No. EP20090748260, dated Jul. 25, 2017, 3 pages.
Third Party Observation for European Application No. EP20090748260, dated Aug. 14, 2017, 8 pages.
Communication pursuant to Rule 114(2) EPC for European Application No. 17175191.0-1111, dated Mar. 2, 2018.

* cited by examiner

FACTOR IX POLYPEPTIDE MUTANT, ITS USES AND METHOD FOR ITS PRODUCTION

This U.S. non-provisional application is a continuation of U.S. application Ser. No. 14/981,981, filed on Dec. 29, 2015, which is a continuation of U.S. application Ser. No. 13/063,898 filed on May 31, 2011, now U.S. Pat. No. 9,249,405, which is a U.S. National Stage of PCT/EP2009/061935, filed 15 Sep. 2009, which claims priority to and the benefit of Italian Application No. BO2009A000275, filed on 6 May 2009 and of Italian Application No. BO2008A000564, filed on 15 Sep. 2008, the contents of which are all incorporated herein by reference in their entireties.

REFERENCE TO AN ELECTRONIC SEQUENCE LISTING

The contents of the electronic sequence listing (Date of Creation: Aug. 31, 2017) are herein incorporated by reference in their entirety.

FIELD OF THE INVENTION

The present invention relates to a modified FIX (factor IX) polypeptide, a nucleotide sequence, a vector comprising said nucleotide sequence and a method for producing the modified FIX polypeptide.

The present invention also relates to pharmaceutical preparations and uses of modified factor FIX and of the nucleotide sequence.

PRIOR ART

FIX is a vitamin K-dependent glycoprotein belonging to the serine-protease family, and is synthesized in the liver of man and other animals, including mammals, playing a fundamental role in both intrinsic and extrinsic pathways of the coagulation cascade. Human FIX circulates in plasma as a single chain zymogen composed of 415 amino acids. Human FIX has a molecular weight of 56 kD and a plasma concentration of about 5 µg/ml. The zymogen is activated both by activated factor XI (FXIa), and tissue factor complex (TF)-activated factor VII (FVIIa). The structural organization of FIX is similar to that of other vitamin K-dependent coagulation proteins such as factor VII (FVII), factor X (FX) and protein C (PC). The amino-terminal portion of the molecule comprises the "Gla" domain, a region rich in gamma-carboxy-glutamic residues whose carboxylation is dependent on the presence of vitamin K. The main physiological function of FIX, once activated, is to convert factor X (FX) into activated factor X (FXa) in a process that requires the presence of a phospholipid surface, calcium ions and a protein with cofactor effect, namely activated factor VIII (FVIIIa). FXa itself is able to convert prothrombin into thrombin which transforms fibrinogen into soluble fibrin which, on polymerization, forms the clot. The action of FXa is enhanced by the presence of activated factor V (FVa).

The human FIX gene is located on chromosome X in position Xq27.1 and contains 8 exons of lengths varying from 25 base pairs (bp) to 2000 bp. Human FIX mRNA is about 3 kb in length and comprises 205 bases which form the 5' UTR region, 1386 bases which encode the FIX polypeptide and 1392 bases of the 3' UTR region. This mRNA encodes the synthesis of 461 amino acids which form the human FIX precursor. This precursor (SEQ ID NO: 1) comprises the following segments and domains: a hydrophobic signal peptide (amino acids 1-28), a propeptide (amino acids 29-46), a Gla-domain (amino acids 47 to 92), an EGF-like 1 domain (amino acids 93 to 129), an EGF-like 2 domain (amino acids 130 to 171), an activation peptide (amino acids 192 to 226) and a serine-protease domain (amino acids 227 to 461). The mature form of human FIX (SEQ ID NO: 2) loses the hydrophobic signal peptide and the propeptide. Consequently the corresponding amino acid positions of the aforementioned domains become the following: a Gla-domain (amino acids 1 to 46), an EGF-like 1 domain (amino acids 47 to 83), an EGF-like 2 domain (amino acids 84 to 125), an activation peptide (amino acids 146 to 180) and a serine-protease domain (amino acids 181 to 415). SEQ ID NO: 1 (from which SEQ ID NO: 2 is derived) corresponds to the sequence on PubMed ("Protein" category) found by entering accession number AAB59620; this amino acid sequence comprises the signal peptide (46 AA), followed by the amino acid sequence of the mature protein.

A genetic deficiency in FIX can cause a number of coagulation diseases (coagulopathies), for example the haemorrhagic disease known as haemophilia B in affected males (sex linked genetic disease). Haemophilia B can be classified into three classes, each of which is characterized by the presence of different plasma concentrations of FIX. In severe haemophilia B the plasma levels of FIX activity are below 1% of normal; in the moderate form, levels are between 1% and 5%; in the mild form, between 5 and 25% of normal levels. There are also healthy carrier individuals who have medium FIX activity levels, between 25% and 50% of normal, but many carriers can have levels even exceeding 50%. Patients affected by severe haemophilia B present serious haemorrhagic manifestations which can be controlled or avoided by administering FIX concentrates of extractive (from human plasma) or of recombinant origin, currently only available in a single commercial formulation.

Attempts to correct the genetic defect by means of gene therapy have so far been fruitless because of various problems. These include firstly those connected to the low efficiency of expression in man of FIX levels in plasma i.e. around 1%, hence not sufficient to correct the disease; those connected to the immunogenicity of treatment with viral vectors; finally those connected to the side effects of gene therapy itself which include hepatitis, myositis and others.

An increase in plasma FIX to higher than normal levels (normal range of FIX in plasma being 70-120% i.e. 70-120 U/dl, where a unit is the quantity of FIX contained in 1 milliliter of normal plasma, equal to about 5 µg) has been associated with an increased risk in humans of developing thrombotic manifestations in the venous system. In particular, for values above 150 U/dl, a 4.8 fold increase in thrombotic risk has been noted (corrected O. R. 4.8; 95% CI, from 2.3 to 10.1). However, the genetic basis for the increased FIX levels in plasma of these individuals has never been identified.

In vitro mutagenesis studies of mutated recombinant FIX expression have demonstrated the possibility of reproducing the alterations in FIX synthesis and activity encountered in vivo in patients with haemophilia B. Vice-versa, by site-specific mutagenesis in certain positions on the FIX molecule, FIX mutants have been produced with "gain-of-function" (increased activity relative to the normal molecule) by altering their specificity for physiological substrates and/or modifying their other functions. In WO 99/03496 is disclosed the recombinant FIX arginine 338 alanine mutant which resulted in a gain-of-function whose activity levels are 2-3 folds higher than that found in wild type FIX. These gain-of-function mutants (in particular with increased protease activity towards the physiological substrate, i.e. FX, or with an increased capacity for interaction with FVIIIa, a cofactor of FIXa) have not as yet been found to exist in nature, nor have they been tested in man. More explicitly, there is no evidence of: 1) the existence of a human carrier of mutated FIX (natural FIX mutant) with gain-of-function characterized by increased functional activity as compared to normal FIX (WT) with any gain-of-function in functional activity; 2) tests conducted in vivo in man with administrations of modified recombinant FIX; 3) tests conducted in vivo in man with administrations of modified recombinant FIX with gain-of-function for the prophylaxis and treatment of patients affected by haemophilia (genetic or acquired) or other coagulopathies; 4) tests conducted in vivo in man with administrations of modified recombinant FIX which show the absence of side effects.

SUMMARY OF THE INVENTION

The object of the present invention is to provide a modified FIX polypeptide, a nucleotide sequence, a vector comprising said nucleotide sequence, and a method for producing the modified FIX polypeptide.

A further object of the present invention is to provide pharmaceutical preparations and uses for modified factor FIX and the nucleotide sequence.

DETAILED DESCRIPTION OF THE INVENTION

According to the present invention are provided polypeptides, nucleotide sequences, vectors, a method of production, uses of the polypeptides and nucleotide sequences and the pharmaceutical preparations, according to that described in the following independent claims and preferably in any one of the claims that depend directly or indirectly on the independent claims.

The modified FIX polypeptides herein described show a gain-of-function of at least 5 folds higher than that of the wild-type FIX molecule. This increase in the activity level is unexpectedly even higher than that disclosed for the known recombinant FIX arginine 338 alanine mutant.

The contents of the references (articles, textbooks, GenBank sequences etc.) cited in the present text are fully included herein for descriptive completion. In particular, the references (articles, textbooks, GenBank sequences etc.) cited in the present text are incorporated herein for reference.

Unless otherwise explicitly specified, the following terms have the meanings indicated below.

In the present text the term "percentage identity" and "% identity" between two amino acid (peptide) or nucleic acid (nucleotide) sequences means the percentage of identical amino acid or nucleotide residues in corresponding positions in the two optimally aligned sequences.

To determine the "percentage identity" of the two amino acid or nucleic acid sequences, the sequences are aligned together. To achieve an optimal match, gaps can be introduced into the sequence (i.e. deletions or insertions which can also be placed at the sequence ends). Amino acid and nucleotide residues in the corresponding positions are then compared. When a position in the first sequence is occupied by the same amino acid or nucleotide residue that occupies the corresponding position in the second sequence, the molecules are identical in that position. The percentage identity between two sequences is a function of the number of identical positions divided by the sequences [i.e. % identity=(number of identical positions/total number of positions)×100] According to an advantageous embodiment, the sequences have the same length.

Advantageously, the compared sequences do not have gaps (or insertions). The percentage identity can be obtained by using mathematical algorithms. A non-limiting example of an algorithm used for comparing two sequences is the Karlin and Altschul algorithm [Proc. Natl. Acad. Sci. USA 87 (1990) 2264-2268] modified by Karlin and Altschul [Proc. Natl. Acad. Sci. USA 90 (1993) 5873-5877]. Said algorithm is incorporated in the BLASTn and BLASTp programmes of Altschul [Altschul et al, J. Mol. Bio. 215 (1990) 403-410].

With the purpose of achieving alignments even in the presence of one or more gaps (or insertions) methods may be used which assign a relatively high penalty for each gap (or insertion) and a lower penalty for each additional amino acid or nucleotide residue in the gap (this additional amino acid or nucleotide residue is defined as gap extension). High penalties will obviously lead to the alignments being optimized with the least number of gaps.

An example of a programme able to achieve this type of alignment is the BLAST programme as described in Altschul et al., Nucleic Acids Res. 25 (1997) 3389-3402. For this purpose the BLASTn and BLASTp programmes can be used with the default parameters. When using the BLAST programme the BLOSUM62 matrix is typically employed.

An advantageous and non-limiting example of a programme for achieving an optimal alignment is GCG Wisconsin Bestfit package (University of Wisconsin, USA; Devereux et. al., 1984, Nucleic Acid Research 12:387). The default parameters are again used i.e. for an amino acid sequence they allow a penalty of −12 for a gap and a penalty of −4 for each extension.

In the present text the term "percentage homology" and "% homology" between two amino acid or nucleotide sequences means the percentage of homologous amino acid or nucleotide residues in corresponding positions in the two optimally aligned sequences.

The percentage homology between two sequences is determined in a substantially identical manner to that described above for determining percentage identity except for the fact that homologous positions and not only identical positions are considered in the calculation.

With regard to a nucleotide sequence, two homologous positions present two different nucleotides but which, within their codon, code for the same amino acid. With regard to an amino acid sequence, two homologous positions present two homologous amino acids, that is to say amino acids possessing similar physico-chemical properties, for example amino acids belonging to the same groups such as: aromatic (Phe, Trp, Tyr), acids (Glu, Asp), polar (Gln, Asn), basic (Lys, Arg, His), aliphatic (Ala, Leu, Ile, Val), with a hydroxyl group (Ser, Thr), with a short side chain (Gly, Ala, Ser, Thr, Met). It is expected that substitutions between these homologous amino acids would not change the phenotype of the proteins (conservative amino acid substitutions). Specific examples of conservative substitutions are known in this technical field and are described in the various literature (e.g. Bowie et al., Science, 247:1306-1310 (1990)).

Further examples of programmes and/or articles relating to the determination of alignments and percentage homologies and/or identities are indicated in, for example, US2008003202, US2007093443, WO06048777.

In the present text the term "corresponding position" means a position in a polypeptide or nucleic acid sequence which, following an alignment, corresponds to (or faces), a precise position in a reference sequence. For example, a position corresponding to a precise position on the FIX polypeptide presenting SEQ ID NO: 2 can be determined by aligning the SEQ ID NO: 2 with a polypeptide of interest; the alignment can be carried out manually or as explained above in relation to percentage identity determination.

In the present text the term "naked chain" means a polypeptide which has not been chemically modified but contains only covalently bound amino acids.

In the present text the term "promoter" means a DNA portion of a gene that controls (activates) the transcription of a nucleotide sequence to which it is operatively linked (but not necessarily flanking it). The promoter includes one or more DNA sequences, which are recognized by RNA polymerase and bind RNA polymerase so that RNA polymerase itself initiates transcription.

In the present text the term "treat" or "treatment" of a pathology means the prophylaxis and/or therapy and/or cure of this pathology. The term prophylaxis means advantageously to at least partially arrest the development of a potential disease and/or to prevent the worsening of symptoms or progression of a disease. Advantageously, the term therapy means a partial or total alleviation of the disease symptoms.

In the present text the term "vector" means an element used to introduce a nucleic acid into a cell for the expression or replication of said nucleic acid. An example of vectors are episomes, which are capable of extra-chromosomal replication. The vectors can also be integrated into host chromosomes. Vectors are often in the form of plasmids, generally circular double-helical DNA.

In the present text "vehicle presenting a nucleic acid" means: a vector which includes nucleic acid; a cell which includes nucleic acid; or a pharmaceutically acceptable excipient combined with the nucleic acid by mixing. Advantageously the vehicle is chosen from a vector or a cell.

According to a first aspect of the present invention, a modified FIX polypeptide is provided comprising an amino acid chosen from the group consisting of: leucine, cysteine, aspartic acid, glutamic acid, histidine, lysine, asparagine, glutamine, tyrosine in a position corresponding to position 338.

According to other embodiments, the amino acid is chosen from the group consisting of: leucine, aspartic acid, glutamine.

According to other embodiments, the amino acid is chosen from the group consisting of: aspartic acid, glutamine.

According to other embodiments, the amino acid is aspartic acid.

According to other embodiments, the amino acid is glutamine.

According to other embodiments, the amino acid is chosen from the group consisting of: aspartic acid, leucine.

According to other embodiments, the amino acid is chosen from the group consisting of: leucine, glutamine.

According to other embodiments, the amino acid is leucine.

The modified FIX polypeptide must be able to carry out its function within the coagulation cascade and can be of synthetic or natural origin, for example human or animal origin.

Examples of FIX polypeptides include (but are not limited to) unmodified wild-type FIX (such as the polypeptide of SEQ ID NO: 2), precursors of said wild-type FIX (such as the polypeptide of SEQ ID NO: 1), natural polymorphic variants (such as: a polypeptide presenting an alanine in a position corresponding to position T148 or to a precursor polypeptide thereof).

In the present text the loci (positions) of the modified or unmodified amino acid sequences are identified by reference to the amino acid numbering in the corresponding positions of an unmodified mature FIX polypeptide, as identified by SEQ ID NO: 2. Corresponding positions can be determined by alignment of unmodified residues (see above). By way of example we report hereinafter the sequences and relative numberings of the mature FIX polypeptide (SEQ ID NO: 2) and of the FIX polypeptide precursor (SEQ ID NO:1).

```
                                        SEQ ID NO: 1
MQRVNMIMAE SPGLITICLL GYLLSAECTV FLDHENANKI

LNRPKRYNSG KLEEFVQGNL ERECMEEKCS FEEAREVFEN

TERTTEFWKQ YVDGDQCESN PCLNGGSCKD DINSYECWCP

FGFEGKNCEL DVTCNIKNGR CEQFCKNSAD NKVVCSCTEG

YRLAENQKSC EPAVPFPCGR VSVSQTSKLT RAEAVFPDVD

YVNSTEAETI LDNITQSTQS FNDFTRVVGG EDAKPGQFPW

QVVLNGKVDA FCGGSIVNEK WIVTAAHCVE TGVKITVVAG

EHNIEETEHT EQKRNVIRII PHHNYNAAIN KYNHDIALLE

LDEPLVLNSY VTPICIADKE YTNIFLKFGS GYVSGWGRVF

HKGRSALVLQ YLRVPLVDRA TCLRSTKFTI YNNMFCAGFH

EGGRDSCQGD SGGPHVTEVE GTSFLTGIIS WGEECAMKGK

YGIYTKVSRY VNWIKEKTKL T in bold underlined Arg 384 corresponding to Arg
338 in SEQ ID NO: 2
                                        SEQ ID NO: 2
YNSGKLEEFV QGNLERECME EKCSFEEARE VFENTERTTE

FWKQYVDGDQ CESNPCLNGG SCKDDINSYE CWCPFGFEGK

NCELDVTCNI KNGRCEQFCK NSADNKVVCS CTEGYRLAEN

QKSCEPAVPF PCGRVSVSQT SKLTRAETVF PDVDYVNSTE

AETILDNITQ STQSFNDFTR VVGGEDAKPG QFPWQVVLNG

KVDAFCGGSI VNEKWIVTAA HCVETGVKIT VVAGEHNIEE

TEHTEQKRNV IRIIPHHNYN AAINKYNHDI ALLELDEPLV

LNSYVTPICI ADKEYTNIFL KFGSGYVSGW GRVFHKGRSA

LVLQYLRVPL VDRATCLRST KFTIYNNMFC AGFHEGGRDS

CQGDSGGPHV TEVEGTSFLT GIISWGEECA MKGKYGIYTK

VSRYVNWIKE KTKLT
in bold underlined Arg 338.
```

Likewise, the positions of the modified or unmodified nucleotide sequences are identified, unless otherwise indicated, by reference to the nucleotide numbering in the corresponding positions of the nucleotide sequence identified by accession number K02402 (GenBank). The nucleotide sequence K02402 codes for the FIX polypeptide precursor (SEQ ID NO: 1) and includes some intron regions (in this regard see Anson D S, Choo K H, Rees D J, Giannelli F, Gould K, Huddleston J A, Brownlee G G. The gene structure of human anti-haemophilic factor IX. The EMBO Journal 1984; 3:1053-1060).

Included within the definition of a modified FIX polypeptide are chimeric variants which can be produced by replacing amino acids or entire domains of the FIX with amino acids or sequences of other factors belonging to the coagulation factor family (for example factor VII or factor X).

According to other embodiments, the modified FIX polypeptide presented herein is either a naked chain or exhibits post-transcriptional modifications. Examples of modifications include one or more chemical modifications, which comprise (but are not limited to): glycosylation, acylation, methylation, phosphorylation, sulphation, carboxylation, salification, vitamin C-dependent modifications such as hydrolysis of proline, aspartic acid, lysine, or carboxy-terminal amidation; vitamin K-dependent modifications such as carboxylation of glutamic acid residues; incorporation of selenium to form one or more selenocysteine(s); incorporation of a PEG moiety (polyethylene glycol).

In addition to the possible modifications disclosed herein, the modified FIX polypeptide can contain one or more variants known in the state of the art such as hyperglycosylation, deimmunization and others (see for example: U.S. Pat. No. 6,277,618, U.S. Pat. No. 6,315,995, U.S. Pat. No. 6,531,298, US2004/0102388, US2004/0110675, US2004/0254106, US2005/0100982, US2006/0040856).

Non-limiting examples of modified FIX polypeptide variants can be deduced from one or more of the following references: US2006/040856, Friedler et al (2000) J. Biol Chem. 275:23783-23789, US2004/102388, WO2006/018201, Lim et al. (1990) J. Biol Chem. 265(1), 144-150, Cheung et al. (1992) J. Biol. Chem. 267(29): 20529-20531, Gui et al. (2002) Blood 100(1):153-158, Schuettrumpf et al. (2005) Blood 105(6): 2316-2323, US2004/110675, U.S. Pat. No. 6,315,995.

According to some alternative embodiments, the modified FIX polypeptide has at least 50%, 60%, 70%, 80%, 85%, 90%, 94%, 97%, 99%, 100% homology (or, advantageously, identity) with a peptide sequence chosen from the group consisting of: SEQ ID NO: 1 and SEQ ID NO: 2.

Advantageously, the modified FIX polypeptide has at least 60% homology (or, advantageously, identity) with a peptide sequence chosen from the group consisting of: SEQ ID NO: 1 and SEQ ID NO: 2.

Advantageously, the modified FIX polypeptide has at least 80% homology (or, advantageously, identity) with a peptide sequence chosen from the group consisting of: SEQ ID NO: 1 and SEQ ID NO: 2.

Advantageously, the modified FIX polypeptide has at least 90% homology (or, advantageously, identity) with a peptide sequence chosen from the group consisting of: SEQ ID NO: 1 and SEQ ID NO: 2.

Advantageously, the peptide sequence is SEQ ID NO: 2.

According to a second aspect of the present invention, a nucleotide sequence is provided which codes for the FIX polypeptide of the first aspect of the present invention.

According to some alternative embodiments, the nucleotide sequence has at least 50%, 60%, 70%, 80%, 85%, 90%, 94%, 97%, 99%, 100% homology (or, advantageously, identity) with the sequence having accession number K02402 (GenBank).

Advantageously, the nucleotide sequence has at least 70% homology (or, advantageously, identity) with the sequence having accession number K02402 (GenBank).

Advantageously, the nucleotide sequence has at least 90% homology (or, advantageously, identity) with the sequence having accession number K02402 (GenBank).

Advantageously, the nucleotide sequence has at least 100% homology (or, advantageously, identity) with the sequence having accession number K02402 (GenBank).

According to some alternative embodiments, the nucleotide sequence is a RNA sequence and has at least 50%, 60%, 70%, 80%, 85%, 90%, 94%, 97%, 99%, 100% homology (or, advantageously, identity) with the sequence from position 31 to position 1411 (SEQ ID NO: 3) (advantageously from position 169 to position 1411—SEQ ID NO: 4) of the polynucleotide of FIG. 2 in the article by Anson D S, Choo K H, Rees D J, Giannelli F, Gould K, Huddleston J A and Brownlee G G. The gene structure of human anti-hemophilic factor IX. The EMBO Journal 1984; 3: 1053-1060. In this case (that is, with reference to SEQ ID NO: 3 and SEQ ID NO: 4), the position numbers refer to the numbering reported in the aforementioned FIG. 2.

Advantageously, the RNA sequence has at least 80% homology (or, advantageously, identity) with the sequence SEQ ID NO: 3 (advantageously, SEQ ID NO: 4). Advantageously, the RNA sequence has at least 90% homology (or, advantageously, identity) with the sequence SEQ ID NO: 3 (advantageously, SEQ ID NO: 4). Advantageously, the RNA sequence has at least 95% homology (or, advantageously, identity) with the sequence SEQ ID NO: 3 (advantageously, SEQ ID NO: 4).

The RNA sequence can be linked, at the head and/or tail, to additional nucleotide chains that are either not translated or translated separately.

According to some alternative embodiments, the nucleotide sequence is a DNA sequence and comprises (in particular, consists of) intron and exon portions, which present an overall sequence (that is to say exon portions without gaps and linked together in order) having at least 50%, 60%, 70%, 80%, 85%, 90%, 94%, 97%, 99%, 100% homology (or, advantageously, identity) with the overall sequence of exon regions in the sequence (SEQ ID NO: 5) of FIG. 4 in the article by Anson D S, Choo K H, Rees D J, Giannelli F, Gould K, Huddleston J A and Brownlee G G. The gene structure of human anti-hemophilic factor IX. The EMBO Journal 1984; 3:1053-1060.

Advantageously, the exon portions are separate from each other and placed in order (arranged relative to each other) as are the respective exon regions in the sequence SEQ ID NO: 5. Advantageously, the overall sequence of the exon portions has at least 80% homology (or, advantageously, identity) with the overall sequence of the exon regions. Advantageously, the overall sequence of the exon portions has at least 90% homology (or, advantageously, identity) with the overall sequence of the exon regions. Advantageously, the overall sequence of the exon portions has at least 95% homology (or, advantageously, identity) with the overall sequence of the exon regions.

According to some embodiments, the nucleotide sequence comprises a thymine in a position corresponding to position 34099 (or in the corresponding position 32318 according to the numbering given in SEQ ID NO: 5; or in the corresponding position 31134 according to the numbering given in the Database of mutations of Hemophilia B (Giannelli et al., Hemophilia B: Database of point mutations and short additions and deletions. Nucleic Acids Research 1990; 18:4053-9); or a uracil in the corresponding position 11180 of SEQ ID NO: 3 or SEQ ID NO: 4).

In other words, the aforementioned nucleotide sequence differs from the sequence having accession number K02402 (GenBank) by at least the fact of bearing a mutation from guanine to thymine in position 34099 (G34099T) or in a corresponding position (for example position 32318 according to the numbering of SEQ ID NO: 5; or from guanine to uracil in the corresponding position 11180 of SEQ ID NO: 3 or SEQ ID NO: 4).

In this case the nucleotide sequence codes for a leucine in a position corresponding to position 338.

According to some embodiments, the nucleotide sequence in the positions corresponding to 34098, 34099 and 34100, presents a triplet chosen from the group consisting of: TTA, UUA, TTG, UUG, CTT, CUU, CTC, CUC, CTA, CUA, CTG, CUG, GAT, GAU, GAC, CAA, CAG. In particular, when the nucleotide sequence is a DNA sequence, the triplet is chosen from the group consisting of TTA, TTG, CTT, CTC, CTA, CTG, GAT, GAC, CAA, CAG.

According to some embodiments, the nucleotide sequence, in the positions corresponding to 34098, 34099 and 34100, presents a triplet chosen from the group consisting of: TTA, UUA, TTG, UUG, CTT, CUU, CTC, CUC, CTA, CUA, CTG, CUG, CAA, CAG. In particular, when the nucleotide sequence is a DNA sequence, the triplet is chosen from the group consisting of TTA, TTG, CTT, CTC, CTA, CTG, CAA, CAG. In these cases, the sequence codes for a leucine or a glutamine in a position corresponding to position 338.

According to some embodiments, the nucleotide sequence, in the positions corresponding to 34098, 34099 and 34100, presents a triplet chosen from the group consisting of: TTA, UUA, TTG, UUG, CTT, CUU, CTC, CUC, CTA, CUA, CTG, CUG. In particular, when the nucleotide sequence is a DNA sequence, the triplet is chosen from the group consisting of TTA, TTG, CTT, CTC, CTA, CTG.

Advantageously, the triplet is CTA. In these cases, the sequence codes for a leucine in a position corresponding to position 338.

According to some embodiments, the nucleotide sequence, in the positions corresponding to 34098, 34099 and 34100, presents a triplet chosen from the group consisting of: CAA, CAG. In these cases, the sequence codes for a glutamine in a position corresponding to position 338. Advantageously, the triplet is CAA. To obtain the CAA triplet, an adenine is inserted in place of the guanine in position 34099.

According to some embodiments, the nucleotide sequence, in the positions corresponding to 34098, 34099 and 34100, presents a triplet chosen from the group consisting of: GAT, GAU, GAC, CAA, CAG. In particular, when the nucleotide sequence is a DNA sequence, the triplet is chosen from the group consisting of GAT, GAC, CAA, CAG. In these cases, the sequence codes for an aspartic acid or a glutamine in a position corresponding to position 338.

According to some embodiments, the nucleotide sequence, in the positions corresponding to 34098, 34099 and 34100, presents a triplet chosen from the group consisting of: GAT, GAU, GAC. In particular, when the nucleotide sequence is a DNA sequence, the triplet is chosen from the group consisting of GAT, GAC. In these cases, the sequence codes for an aspartic acid in a position corresponding to position 338. Advantageously, the triplet is GAT. To obtain the GAT triplet, a guanine is inserted in place of the adenine in position 34098, an adenine in place of the guanine in position 34099 and a thymine in place of the adenine in position 34100.

The aforesaid homology (or identity) percentages are calculated without considering the specific mutated positions indicated. In other words, for example, the sequence SEQ ID NO: 2 modified with a leucine in position 338 is considered as having 100% homology (and identity) with the unmodified sequence SEQ ID NO: 2.

According to a third aspect of the present invention, a nucleic acid is provided which comprises a nucleotide sequence according to the second aspect of the present invention.

According to some embodiments, the nucleic acid comprises a promoter in operational linkage with the nucleotide sequence.

According to a fourth aspect of the present invention, a vector is provided comprising a nucleic acid as aforedefined in relation to the third aspect of the present invention. In particular, the vector comprises a nucleotide sequence according to the second aspect of the present invention.

According to some embodiments, the vector is chosen from: a prokaryote vector, a eukaryote vector or a viral vector.

Advantageously, the vector is a viral vector. In particular, the vector is chosen from: an adenovirus, a retrovirus, a herpesvirus, a lentivirus, a poxvirus, a cytomegalovirus.

According to a fifth aspect of the present invention, a method for the production of a modified FIX polypeptide is provided, whereby the modified FIX polypeptide is expressed by means of a nucleic acid according to the third aspect of the present invention.

According to some embodiments the method comprises the steps of: introducing a vector of the fourth aspect of the present invention into a cell; and culturing the cell such that the FIX polypeptide is expressed.

Alternatively, the modified FIX polypeptide can be produced by a host animal or in vitro from the aforementioned nucleotide sequence.

According to a particular aspect of the present invention, the method comprises the steps of: introducing the nucleotide sequence of the second aspect of the present invention into a cell-free system; expressing the modified polypeptide in the cell-free system.

According to a further particular aspect of the present invention, the method allows the modified FIX polypeptide to be expressed in a transgenic animal comprising a nucleic acid in accordance with the third aspect of the present invention (in particular, the nucleotide sequence of the second aspect of the present invention). Useful hosts for expression of the modified FIX polypeptide include: *E. coli*, yeasts, plants, insect cells, mammalian cells (Pham et al. (2003) Biotechnol. Bioeng. 84:332-42; Bon et al. (1998) Semin Hematol. 35 (2 Suppl 2): 11-17; Wahij et al., J. Biol. Chem. 280 (36) 31603-31607) and transgenic animals.

The hosts can vary as to their levels of protein production and also the types of modifications induced in the modified FIX polypeptide subsequent to transcription. Eukaryote hosts can include yeasts such as *Saccharomyces cerevisiae* and *Pichia pastoris* (Skoko et al. (2003) Biotechnol. Appl. Biochem. 38 (Pt 3): 257-65), insect cells (Muneta et al. (2003) J. Vet. Med. Sci. 65(2): 219-23), plants and cells from plants such as tobacco, rice, algae (Mayfield et al. (2003) PNAS 100:438-442) etc. The plants are typically modified by direct transfer of DNA and *agrobacterium*-mediated transformations. Advantageously usable vectors comprise promoter sequences and transcription termination and control elements.

Yeasts are usually modified by replicating episomal vectors or by a stable chromosomal integration by homologous recombination. Advantageously, promoters are used to regulate gene expression. Examples of promoters include GAL1, GAL7, GAL5, CUP1. Proteins produced by yeasts are usually soluble; alternatively, proteins expressed in yeasts can be secreted.

Expression in eukaryotic hosts also includes production in animals, for example in serum, milk and eggs. Transgenic animals for the production of FIX polypeptides are known (for example US2002/0166130 and US2004/0133930) and can be adapted for producing the modified FIX polypeptide as aforedefined.

Prokaryote cells in particular *E. coli* can be advantageously utilized to produce large quantities of modified FIX polypeptide as aforedefined (Platis et al. (2003) Protein Exp. Purif. 31(2):222-30; Khalizzadeh et al. (2004) J. Ind. Microbiol. Biotechnol. 31(2): 63-69).

The vectors used with *E. coli* advantageously contain promoters able to induce high levels of protein expression and to express proteins that show some toxicity towards the host cells. Examples of promoters are T7 and SP6 RNA.

Reducing agents such as β-mercaptoethanol can be utilized to solubilise polypeptides which may precipitate in the cytoplasmic environment of *E. coli*.

According to a sixth aspect of the present invention, a modified FIX polypeptide is also provided in accordance with the first aspect of the present invention, for use as a medicament.

The modified FIX polypeptide can be used for disease treatments either alone or in combination with other active compounds.

The modified FIX polypeptide is useful for treating coagulopathies (congenital or acquired), haematological diseases (congenital or acquired), haemorrhagic disorders (such as haemorrhagic gastritis and/or uterine bleeding), other cardiovascular diseases According to some embodiments, the modified FIX polypeptide is provided for the treatment of at least one coagulopathy.

According to some embodiments, the modified FIX polypeptide is provided for the treatment of haematological diseases.

According to some embodiments, the modified FIX polypeptide is provided for the treatment of haemorrhagic disorders.

According to some embodiments, the modified FIX polypeptide is administered to patients periodically for relatively long time periods or before, during and/or after surgical procedures to reduce and/or prevent haemorrhages.

The use of modified FIX polypeptide for the treatment of coagulopathies is particularly effective.

Advantageously, modified FIX polypeptide is used for the treatment of haemophilia, and in particular haemophilia A and haemophilia B.

According to advantageous embodiments, the modified FIX polypeptide is provided for treating haemophilia B, and advantageously severe and/or moderate haemophilia B.

Advantageously, modified FIX polypeptide is used for the treatment of mammals, in particular human patients.

According to a seventh and an eighth aspect of the present invention, the following are provided: use of the modified FIX polypeptide in accordance with the first aspect of the present invention for preparing a drug (pharmaceutical preparation) advantageously for treating a coagulopathy; and a pharmaceutical preparation comprising the modified FIX polypeptide and, advantageously, at least one pharmaceutically acceptable excipient.

According to some embodiments, the pharmaceutical preparation is for the treatment of a pathology chosen from the group consisting of: coagulopathies (congenital or acquired), haematological diseases (congenital or acquired), haemorrhagic disorders (such as haemorrhagic gastritis and/or uterine bleeding), haemophilia (haemophilia A or haemophilia B). According to specific embodiments, the pharmaceutical preparation is for treating a coagulopathy.

According to specific embodiments, the pharmaceutical preparation is for treating haemophilia.

According to a further aspect of the present invention, a method is provided for treating at least one coagulopathy, this method allowing the administration of an effective quantity of a modified FIX polypeptide as aforedefined.

The modified FIX polypeptide can be administered as a pure compound, but is advantageously presented in the form of a pharmaceutical preparation. Non-limiting examples of pharmaceutical preparations if needed for this purpose are explained below.

The modified FIX polypeptide can be formulated for oral, parenteral or rectal administration, or in forms suited to administrations by inhalation or insufflation (either via the mouth or nose). Formulations for oral or parenteral administration are advantageous.

For oral administrations, the pharmaceutical preparations are in the form of, for example, tablets or capsules prepared by known methods with pharmaceutically acceptable excipients such as binders (for example pregelatinized maize starch, polyvinylpyrrolidone, or methyl cellulose); fillers (for example lactose, microcrystalline cellulose or calcium hydrogen phosphate); additives (for example magnesium stearate, talc, silica); disintegrants (for example potato starch); and/or lubricants (for example sodium lauryl sulphate). The tablets can be coated using known methods. Liquid preparations for oral administration have the form, for example, of solutions, syrups or suspensions, or can be in the form of a dry product that can be dissolved in water or another liquid prior to use. Said preparations are prepared by known methods with pharmaceutically acceptable additives such as suspending agents (for example sorbitol, cellulose derivatives, edible hydrogenated fats); emulsifying agents (for example lecithin or acacia); non-aqueous liquids (for example almond oil, oily esters, ethyl alcohol or fractionated vegetable oils); and/or preservatives (for example methyl or propyl-hydroxybenzoates, sorbic acid or ascorbic acid). The preparations can also contain, in appropriate cases, buffering salts, colouring agents, flavouring agents and/or sweeteners.

Preparations for oral administration are formulated in a known manner, in order to provide a controlled release of the active compound.

The modified FIX polypeptide is formulated, in a known manner, for parenteral administration, by injection or continuous administration. Formulations for injection are, advantageously, in the form of dosage units, for example in ampoules or multi-dose containers containing preservatives. The composition can be in the form of a suspension, in aqueous or oily liquids, and can contain elements of the formulation as dispersing and stabilizing agents. Alternatively, the active compound can be in powder form to be dissolved just before use in a liquid as needed, such as sterile water.

The modified FIX polypeptide can be formulated for rectal administration as suppositories or enemas, for example, containing suppository excipients of known type such as cocoa butter or other glycerides.

The modified FIX polypeptide is also formulated, in a known manner, in extended release compositions. These extended release compositions are, for example, administered by means of an implant (for example subcutaneous or intramuscular) or an intramuscular injection. Therefore, for example, the modified FIX polypeptide is formulated with suitable polymer or hydrophobic materials (such as an emulsion or an oil) or ion exchange resins, or relatively poorly soluble derivatives, such as relatively poorly soluble salts.

For intranasal administration, the modified FIX polypeptide is formulated by administrations via a (known) device, such as in a powder with a suitable vehicle. The dosages of the modified FIX polypeptide will depend on the patient age and condition, and so the precise dosage will have to be decided each time by the physician. The dosage will also depend on the mode of administration and the particular compound selected. Usable doses can be for example comprised between 0.1 mg/kg and 400 mg/kg body weight per day.

According to a further aspect of the present invention, the nucleotide sequence is provided in accordance with the second aspect of the present invention for use as a medicament (advantageously for treating a coagulopathy).

The nucleotide sequence can be used for treating a pathology either alone or in combination with other active compounds.

The nucleotide sequence is useful for treating the pathologies of the sixth aspect of the present invention.

According to particular aspects of the present invention, the following are provided: the use of the aforementioned nucleotide sequence for preparing a drug advantageously for treating a coagulopathy; and a pharmaceutical preparation containing the nucleotide sequence.

Instead of administering the modified FIX polypeptide it is possible to administer the nucleotide sequence which encodes it.

The nucleotide sequence can be inserted into cells or tissues by means of any known method. The nucleotide sequence can be incorporated into a vector for subsequent manipulations.

For example, certain cells could be engineered so as to express the modified FIX polypeptide, by integrating the aforementioned nucleotide sequence into a genomic location operatively linked with the promoter sequences. Said cells can be administered to a patient locally or systemically.

Usable viral vectors include poxvirus, herpesvirus, retrovirus, adenovirus, adeno-associated virus and other viruses suitable for gene therapy.

The vectors can remain as episomal or can be integrated into the chromosomes of the treated individual. Adenovirus serotypes are commercially available from the American Type Culture Collection (ATCC, Rockville).

The viral vectors, in particular adenovirus, are used ex vivo; for example, cells are isolated from a patient and transduced with an adenovirus expressing the modified FIX polypeptide. After a suitable period of culturing, the transduced cells are administered to the patient locally or systemically.

Alternatively, the viruses, in particular adenoviruses, which express the modified FIX polypeptide are isolated and formulated with a pharmaceutically acceptable excipient and administered to the patient. Typically, the adenoviruses are administered at doses of 1 to 1014 particles per kilogram of patient weight, generally from 106 to 1012 particles per kilogram of patient weight.

Additional examples of cell types for the expression and release of the modified FIX polypeptide are fibroblasts and endothelial cells (Palmer et al. (1989) Blood 73:483-445; Yao et al (1991) PNAS 88:8101-8105).

A vehicle which presents the aforementioned nucleotide sequence can be formulated in a similar manner to that described above for the modified FIX polypeptide.

The nucleotide sequence and/or drugs and/or vehicles presenting said nucleotide sequence can be used for treating the pathologies referred to above in relation to the modified FIX peptide.

Advantageously, the aforementioned nucleotide sequence is used for treating mammals, in particular human patients.

According to a further aspect of the present invention, a method is provided for detecting the protein of the first aspect of the present invention and/or the nucleotide sequence of the second aspect of the present invention.

Usable methods are those known in the state of the art, and can be adapted to those polymorphism under study to include for example immunoenzymatic assays, coagulation protein activity tests (including FIX activity), coagulometric and chromogenic tests.

According to some embodiments, the method comprises a step of amplifying by PCR part of a nucleic acid molecule (in which it is required to verify the presence of the nucleotide sequence of the second aspect of the present invention).

Advantageously, the amplification step is preceded by a step of purifying, in particular isolating, the nucleic acid molecule.

Advantageously the amplification step is followed by a sequencing step. By way of example, the methods of examples 2 and 3 below can be followed to detect the aforesaid nucleotide sequence.

The method for detecting the protein and/or nucleotide sequence can be used to assist in the identification of those individuals who display a high tendency to develop blood diseases such as thrombosis.

Further characteristics of the present invention will ensue from the following description of some examples which are merely illustrative and non-limiting.

Example 1—Routine Laboratory Tests Carried Out on the Proband

Routine laboratory coagulation tests were carried out with regard to thrombophilia screening on an individual (defined as the Proband) exhibiting episodes of deep vein thrombosis but no other health problems.

In particular, the following were carried out: prothrombin time, partial thromboplastin time, factor IX levels, factor VIII and XI levels, antithrombin levels (activity and antigen), protein C levels (coagulometric and chromogenic activity, antigen), protein S levels (total antigen, free antigen and activity), activated protein C resistance, DNA analysis for factor V Leiden, DNA analysis for the prothrombin variant G20210A, antiphospholipid antibodies, plasminogen, fibrinolysis tests. The coagulation tests carried out on the Proband were all found to be within normal limits except for FIX activity (see example 4 below).

Example 2—Isolation of Mutant FIX from Plasma and from the Cell Culture Medium

Isolation of FIX from plasma or from culture medium was achieved by means of the immunoaffinity column technique, using a resin (sepharose 4B) to which the anti-FIX monoclonal antibody AHIX-5041 [Haematologic Technologies, Inc. (Essex Junction, Vt., USA)] was covalently bound (3.5 mg of monoclonal antibody per 3 ml of sepharose resin). Briefly, the column was equilibrated with buffer containing 20 mM Tris, 150 mM NaCl, 1 mM benzamidine (mM=millimolar). Starting from the plasma, vitamin K-dependent factors were precipitated by adding barium chloride. After centrifugation, the sediment was resuspended in a solution containing 0.2 M EDTA. The preparation thus obtained was extensively dialyzed (2 times, for at least 2 hours) in a solution containing 20 mM Tris, 150 mM NaCl. After dialysis, the preparation was permitted to pass through the column at a rate of 0.5 ml/min. After extensive column washing (10 column volumes) with Tris/NaCl buffer, elution was carried out using a solution of acidic glycine (pH 2.45). The eluate pH was immediately neutralized by adding 2 M Tris at pH 7.5. The eluate fractions containing protein (tested by the Bradford protein assay) were pooled and dialyzed against a Tris-NaCl solution, the FIX was then concentrated through a 200 µl microcolumn of fast-flow sepharose Q (ion exchange). The purity of the preparation was evaluated by applying the silver staining technique on the SDS-PAGE gel.

Example 3—Genetic Study of FIX

PCR amplification and direct sequencing of the exons and splice sites of the Proband FIX gene were carried out using standardized techniques and primers as reported in the literature (From: Methods in Molecular Medicine, Vol 31: Hemostasis and Thrombosis Protocols. Edited by D. J. Perry and K. J. Pasi. Humana Press Inc. Totowa, N.J. Chapter 16: Hemophilia B mutational analysis. By Peter Green). Briefly, amplification was carried out by using intron primer pairs flanking each of the eight exons of the FIX gene. The sequencing was undertaken with an ABI PRISM 310 sequencer (Perkin Elmer, Foster City, Calif.) using the ABI PRISM Big Dye Terminator kit for cycle sequencing reactions. The sequence data were analyzed using the Sequencing Analysis 3.0 programme (Perkin Elmer, Calif.). The sequence obtained was compared with the FIX sequence reported on the GenBank database (accession number: K02402).

Analysis of the nucleotide sequence of the Proband FIX gene has documented a single mutation in exon VIII of the FIX gene compared to the normal sequence. The patient was found to be a carrier for a mutation from G to T at position 34099 of the FIX gene (normal sequence of the FIX gene, Gene bank accession number: K02402) (or in the corresponding position 31134 according to the numbering given in the Database of mutations of Hemophilia B (Giannelli et al., Hemophilia B: Database of point mutations and short additions and deletions. Nucleic Acids Research 1990; 18:4053-9) able to change codon 338 from Arginine to Leucine. Therefore the FIX molecule present in the Proband's plasma (mutated FIX) differs from the normal FIX molecule only by the presence of the amino acid substitution in position 338 where there is a Leucine instead of Arginine.

Example 4—In Vitro Mutagenesis, Expression and Purification of Recombinant FIX Containing the Leu 338 Mutation Site-specific mutagenesis was carried out according to standard techniques described by Kunkel (Kunkel T A. Rapid and efficient site-specific mutagenesis without phenotypic selection; Proc Natl Acad Sci, USA 1985, 82:488-492). Sequencing of the cDNA was carried out for assurance that the mutation was correct and that any new mutations had not been introduced. Expression of the recombinant FIX was obtained using "human embryonic kidney cell line 293" and the methods already reported in the literature (Chang J L, Jin J P, Lollar P, et al. Changing residue 338 in human factor IX from arginine to alanine causes an increase in catalytic activity. J. Biol. Chem. 1998; 273:12089-12094). The recombinant FIX was isolated from the supernatant (culture medium) by means of an immunoaffinity column, as aforedescribed. Briefly, the supernatant of the cell culture was collected every 24 hours for 10 days and conserved at −20° C. For the purification the supernatant was thawed out and benzamidine and EDTA were added to a final concentration of 5 milliMoles and 4 milliMoles respectively. After filtration through a Millipore filter, the supernatant was incubated with fast-flow Sepharose 0 resin for 12 hours at 4° C. The resin was then re-equilibrated in Tris, NaCl and benzamidine buffer and loaded onto the column. Elution was undertaken with a 0-60 nM calcium gradient. The eluate was then dialyzed in a Tris-NaCl buffer. The preparation was then applied to the immunoaffinity column following the method described in example 2 (in the "in vitro" expression of the recombinant protein). Starting from the culture medium, the procedure was the same as for the plasma, except for the precipitation procedure using BaCl. The culture medium was centrifuged at 4000 g for 20 minutes then subjected to dialysis in Tris-NaCl and loaded onto the immunoaffinity column at a rate of 0.5 ml/min.

The remaining steps were the same as those taken for the plasma.

The FIX with the G34099T gene mutation resulting in the 338Leu amino acid substitution, was obtained by in vitro mutagenesis and expression techniques. The level of expression in cell culture was found to be similar to that obtainable with non-mutated recombinant FIX (normal molecule). Specifically, the expression level of the non-mutated recombinant FIX was between 750 and 880 ng/ml while for the recombinant factor IX with the gene mutation G34099T resulting in the 338Leu amino acid substitution, the level was between 590 and 629 ng/ml.

Example 5—Functional Assay of FIX

The functional assay of FIX was carried out on the Proband's plasma with a coagulometric test using Actin (Dade Behring, Marburg, Germany) and FIX deficient plasma (Dade Behring, Marburg, Germany). Briefly for the coagulometric test a variant of the partial thromboplastin time (PTT) was used in a system containing FIX deficient plasma. After adding the calcium chloride the clotting time was measured in seconds. This clotting time was compared to those of a calibration curve obtained by serial dilutions of a pool of normal plasma as reference containing FIX at a quantity of 5 µg/ml (i.e. 100%), and the FIX percentage present in the sample being calculated on 100% of the normal plasma pool (according to common standardized methods).

The normal range for the test had been previously obtained by analyzing, using the same method, 100 healthy individuals of both sexes, aged between 20 and 70 years.

The activity levels of FIX in the Proband were found to be equal to 776% (normal range in 100 healthy individuals, 80-120%).

Example 6—Assay of FIX Antigen

The FIX antigen was determined with the ELISA test using a first anti-FIX monoclonal antibody (Affinity Biologicals, Ontario, Canada) coated (bound) onto the plate for the capture and a second monoclonal antibody labelled with Horseradish peroxidase (HRP) (Affinity Biologicals, Canada) for the detection of FIX. The reference curve was constructed by diluting a pool of normal plasma from 1:100 to 1:3200 in a buffer for the samples, according to standardized procedures. Briefly, the first antibody was bound to the plate after dilution in sodium bicarbonate buffer at basic pH (pH=9.0) at a final concentration of 4 µg/ml. After extensive washing of the plate with Tris-NaCl-Tween20 buffer, the samples, diluted 1:100 and 1:200 in the same buffer, were loaded into the wells and incubated at ambient temperature for 2 hours. After removal of the samples from the wells and extensive washing with the buffer, 100 µl of a solution containing the second antibody conjugated with HRP were added to each of the wells and incubated at ambient temperature for two hours. After further washes, 100 µl of a solution containing tetramethylbenzidine (TMB) were added and the developed color was measured by spectrophotometer with a 450 nanometer filter. The level of FIX antigen was calculated using the reference curve and expressed as a percentage of the pool of normal plasma. The normal test range was previously obtained using the same method by analyzing 100 healthy individuals of both sexes, aged between 20 and 70 years.

FIX antigen levels were found to be equal to 92% (normal range 80-120%). This result (combined with that obtained in example 5) was compatible with the presence of normal quantities of a synthesized circulating FIX, but with its procoagulant function being around 8-9 times greater than the normal FIX molecule.

Example 7—Activity and Antigen Levels of FIX after Reconstitution of a FIX Deficient Plasma with an FIX Extracted from the Proband's Plasma and with Recombinant FIX After isolating FIX from the Proband's plasma, this FIX was used for reconstituting a FIX deficient plasma (Dade-Behring, Milan, Italy) with a final FIX concentration of 5 µg/ml (equal to 100% of normal). The measurements of FIX activity and antigen in the thus reconstituted plasma were 740% and 95% respectively, these being hence comparable with those of the Proband's plasma.

For assaying the activity of the recombinant FIX obtained in accordance with example 4, the same system was used after recomposition of a FIX deficient plasma with a quantity of mutated recombinant FIX (rFIX 338Leu) such as to restore the normal FIX concentration in normal human plasma, i.e. 5 µg/ml (corresponding to 100% of normal) (µg=micrograms). The measurements of recombinant factor IX activity and antigens were 780% and 90% respectively, these being hence comparable with those of the Proband's plasma. This indicates that the recombinant protein thus obtained, containing the amino acid substitution also present in factor IX of the Proband, has a biological activity at least 8-9 times greater than normal factor IX.

Example 8—SDS-PAGE and Immunoblotting of FIX

The SDS-PAGE and immunoblotting (Western blot) of the FIX was carried out on a 5-15% linear gradient gel according to standard procedures. Briefly, the samples containing normal FIX or recombinant FIX were loaded into the polyacrylamide gel wells and subjected to electrophoresis.

The FIX was then subjected to transblotting on a polyvinylidene fluoride (PVDF) membrane using a semidry apparatus (Novablot, GE-Healthcare, Milan, Italy).

The FIX was detected on the PVDF membrane after transblotting using an anti-FIX monoclonal antibody conjugated to HRP (Affinity Biologicals, Ontario, Canada).

SDS-PAGE and immunoblot of a normal FIX polypeptide, a modified FIX polypeptide according to the present invention, and a recombinant modified FIX polypeptide according to the present disclosure show that the FIX isolated from the Proband, the 338Leu recombinant FIX and the normal FIX exhibit the same electrophoretic mobility and the same immunoblot pattern.

Therefore no significant differences (neither quantitative nor qualitative) between normal human FIX, 338 Leu natural mutant human FIX and 338Leu recombinant FIX were found using this technique.

From the aforedescribed, it is clear that the presence of a leucine in a position corresponding to position 338 surprisingly increases the activity of FIX polypeptide by almost eight times.

The present invention proves to be a particular improvement on the state of the art as it provides a modified FIX polypeptide which in vivo in man does not cause any side effects other than an increased coagulation activity.

Example 9—In Vitro Mutagenesis, Expression and Purification of the Recombinant FIX Containing the 338 Asp Mutation (338 Aspartic Acid, 338D)

The site-specific mutagenesis was carried out according to standard techniques described by Kunkel (Kunkel T A. Rapid and efficient site-specific mutagenesis without phenotypic selection; Proc Natl Acad Sci USA 1985, 82: 488-492) by inserting a guanine in place of cytosine in position 34098, and an alanine in place of guanine in position 34099 and a thymine in place of alanine in position 34100 (the mutagenesis was also repeated by inserting a guanine in place of cytosine in position 34098, an adenine in place of guanine in position 34099 and a guanine in place of adenine in position 34100).

Sequencing of the cDNA was carried out for assurance that the mutation was correct and that any new mutations had not been introduced. Expression of the recombinant FIX was obtained using "human embryonic kidney cell line 293" and the methods already reported in the literature (Chang J L, Jin J P, Lollar P, et al. Changing residue 338 in human factor IX from arginine to alanine causes an increase in catalytic activity. J. Biol. Chem. 1998; 273:12089-12094). The recombinant FIX was isolated from the supernatant (culture medium) by means of an immunoaffinity column, as aforedescribed. Briefly, the supernatant of the cell culture was collected every 24 hours for 10 days and conserved at −20° C. For the purification the supernatant was thawed out and benzamidine and EDTA were added to a final concentration of 5 milliMoles and 4 milliMoles respectively. After filtration through a Millipore filter, the supernatant was incubated with fast-flow Sepharose Q resin for 12 hours at 4° C. The resin was then re-equilibrated in Tris, NaCl and benzamidine buffer and loaded onto the column. Elution was undertaken with a 0-60 nM calcium gradient. The eluate was then dialyzed in a Tris-NaCl buffer. The preparation was applied to the immunoaffinity column following the method described in example 2 (in the "in vitro" expression of the recombinant protein). Starting from the culture medium, the procedure was the same as for the plasma, except for the precipitation procedure using BaCl. The culture medium was centrifuged at 4000 g for 20 minutes then subjected to dialysis in Tris-NaCl and loaded onto the immunoaffinity column at a rate of 0.5 ml/min. The remaining steps were the same as those taken for the plasma.

The FIX with the amino acid substitution 338Asp was obtained by in vitro mutagenesis and expression techniques.

The level of expression in cell culture was found to be similar to that obtainable with non-mutated recombinant FIX (normal molecule). Specifically, the expression level of the non-mutated recombinant FIX was between 750 and 880 ng/ml while for the recombinant factor IX with the 338Asp amino acid substitution, the level was between 650 and 740 ng/ml.

Example 10—Activity and Antigen Levels of FIX after Reconstitution of a FIX Deficient Plasma with Recombinant FIX with 338Asp Mutation For the assay of the activity of recombinant FIX obtained in accordance with example 9, the same system was used after recomposition of a FIX deficient plasma with a quantity of mutated recombinant FIX (rFIX 338Asp) such as to restore the normal concentration of FIX in normal human plasma, i.e. 5 µg/ml (corresponding to 100% of normal) (µg=micrograms). Measurements of recombinant factor IX activity and antigens were 460% and 98% respectively. This indicates that the recombinant protein thus obtained (FIX 338 Asp), has a biological activity at least 5 times greater than normal factor IX.

Example 11—SDS-PAGE and Immunoblotting of FIX

The SDS-PAGE and immunoblotting (Western blot) of the FIX was carried out on a 5-15% linear gradient gel according to standard procedures. Briefly, the samples containing normal FIX or recombinant FIX were loaded into the polyacrylamide gel wells and subjected to electrophoresis.

The FIX was then subjected to transblotting on a polyvinylidene fluoride (PVDF) membrane using a semidry apparatus (Novablot, GE-Healthcare, Milan, Italy).

The FIX was detected on the PVDF membrane after transblotting using an anti-FIX monoclonal antibody conjugated to HRP (Affinity Biologicals, Ontario, Canada).

The 338Asp recombinant FIX and the normal FIX exhibit the same electrophoretic mobility and the same immunoblot pattern. Therefore no significant differences (neither quantitative nor qualitative) between normal human FIX and 338Asp recombinant FIX were found using this technique.

From the aforedescribed, it is clear that the presence of an Aspartic acid in a position corresponding to position 338 surprisingly increases the activity of FIX polypeptide by almost eight times.

The present invention proves to be a particular improvement on the state of the art as it provides a modified FIX polypeptide which in vivo in man does not cause any side effects other than an increased coagulation activity.

Example 12—In Vitro Mutagenesis, Expression and Purification of Recombinant FIX Containing the 338Gln Mutation (338 Glutamine, 338Q)

Site-specific mutagenesis was carried out according to standard techniques described by Kunkel (Kunkel T A. Rapid and efficient site-specific mutagenesis without phenotypic selection; Proc Natl Acad Sci USA 1985, 82: 488-492) by inserting an adenine in place of guanine in position 34099 (the mutagenesis was also repeated by inserting an adenine in place of guanine in position 34099, and a guanine in place of adenine in position 34100). Sequencing of the cDNA was carried out for assurance that the mutation was correct and that any new mutations had not been introduced. Expression of the recombinant FIX was obtained using "human embryonic kidney cell line 293" and the methods already reported in the literature (Chang J L, Jin J P, Lollar P, et al. Changing residue 338 in human factor IX from arginine to alanine causes an increase in catalytic activity. J. Biol. Chem. 1998; 273:12089-12094). The recombinant FIX was isolated from the supernatant (culture medium) by means of an immunoaffinity column, as aforedescribed. Briefly, the supernatant of the cell culture was collected every 24 hours for 10 days and conserved at −20° C. For the purification the supernatant was thawed out and benzamidine and EDTA were added to a final concentration of 5 milliMoles and 4 milliMoles respectively. After filtration through a Millipore filter, the supernatant was incubated with fast-flow Sepharose Q resin for 12 hours at 4° C. The resin was then re-equilibrated in Tris, NaCl and benzamidine buffer and loaded onto the column. Elution was undertaken with a 0-60 nM calcium gradient. The eluate was then dialyzed in a Tris-NaCl buffer. The preparation was then applied to the immunoaffinity column following the method described in example 2 (in the "in vitro" expression of the recombinant protein). Starting from the culture medium, the procedure was the same as for the plasma, except for the precipitation procedure using BaCl. The culture medium was centrifuged at 4000 g for 20 minutes then subjected to dialysis in Tris-NaCl and loaded onto the immunoaffinity column at a rate of 0.5 ml/min. The remaining steps were the same as those taken for the plasma.

The FIX with the amino acid substitution 338Gln was obtained by in vitro mutagenesis and expression techniques. The level of expression in cell culture was found to be similar to that obtainable with non-mutated recombinant FIX (normal molecule). Specifically, the expression level of the non-mutated recombinant FIX was between 750 and 880 ng/ml while for the recombinant factor IX with the 338Gln amino acid substitution, the level was between 600 and 720 ng/ml.

Example 13—Levels of Activity and Antigen of the FIX after Reconstitution of a FIX Deficient Plasma with Recombinant FIX with 338Gln Mutation For the assay of the activity of recombinant FIX obtained in accordance with example 12, the same system was used after recomposition of a FIX deficient plasma with a quantity of mutated recombinant FIX (rFIX 338Gln) such as to restore the normal concentration of FIX in normal human plasma, i.e. 5 µg/ml (corresponding to 100% of normal) (µg=micrograms). Measurements of recombinant factor IX activity and antigens were 1360% and 99% respectively. This indicates that the recombinant protein thus obtained (FIX 338 Gln) has a biological activity at least 13 times greater than normal factor IX.

Example 14—SDS-PAGE and Immunoblotting of FIX

The SDS-PAGE and immunoblotting (Western blot) of the FIX was carried out on a 5-15% linear gradient gel according to standard procedures. Briefly, the samples containing normal FIX or recombinant FIX were loaded into polyacrylamide gel wells and subjected to electrophoresis.

The FIX was then subjected to transblotting on a polyvinylidene fluoride (PVDF) membrane using a semidry apparatus (Novablot, GE-Healthcare, Milan, Italy).

The FIX was detected on the PVDF membrane after transblotting using an anti-FIX monoclonal antibody conjugated to HRP (Affinity Biologicals, Ontario, Canada).

The 338Gln recombinant FIX and the normal FIX exhibited the same electrophoretic mobility and the same immunoblot pattern. Therefore no significant differences (neither quantitative nor qualitative) between normal human FIX and 338Gln recombinant FIX were found using this technique.

From the aforedescribed, it is clear that the presence of a glutamine in a position corresponding to position 338 surprisingly increases the activity of FIX polypeptide by almost thirteen times.

The present invention proves to be a particular improvement on the state of the art as it provides a modified FIX polypeptide which in vivo in humans does not cause any side effects other than an increased coagulation activity.

Therefore evidence is provided that:

1) it has been discovered a naturally occurring FIX mutant (arginine 338 leucine) with a 8-9 fold increased functional activity as compared to FIX wild-type;

2) recombinant modified FIX polypeptides (not known before) with 5 folds (FIX arginine 338 aspartic acid), 8 to 9 folds (FIX arginine 338 leucine), 13 folds (FIX arginine 338 glutamine) increased functional (procoagulant) activity, respectively, as compared to FIX wild-type can be generated.

The use of the mutants of the invention, which show such a specific functional activity of 5 folds or above, and in particular 8 to 9 folds as compared to FIX wild type, for medical use and in particular for the prophylaxis and treatment of Hemophilia B patients; said use of the mutants of the invention has never been considered before and is part of the present invention.

The use of the mutants of the invention, which show such a specific functional activity of 5 folds or above, and in particular 8 to 9 folds as compared to FIX wild type, for gene therapy of Hemophilia B patients has never been considered before and is part of the present invention.

The use of the mutants of the invention, which show a specific functional activity of 5 folds or above, and in particular 8 to 9 folds as compared to FIX wild type, for the prophylaxis and treatment of hemorrhagic coagulopathies other than Hemophilia B or for gene therapy of such diseases has never been considered before and is part of the present invention.

It has to be noted that the use of the mutants of the invention, which show a specific functional activity of 5 folds or above, and in particular of FIX arginine 338 leucine which shows 8 to 9 folds increased functional activity as compared to FIX wild type, is considered optimal for the treatment of patients with hemophilia B because of the presence of an identical naturally occurring mutant in humans (never described before, and is part of the present invention) which does not generate neutralizing antibodies. In addition, the FIX functional activity levels express by FIX arginine 338 leucine, is possibly the best option being higher than that of FIX arginine 338 alanine (previously known and described in WO 99/03496, with a modest increase in activity of 2 to 3 folds that of FIX wild-type) and not too high to cause thrombotic complications in hemophilia B patients or patients with other hemorrhagic coagulopathies.

The invention of FIX arginine 338 leucine, is also the best choice for the use of FIX mutants in gene therapy by using viral vectors, given the actual efficiency and yield of the method for the treatment (partial correction) of Hemophilia B.

According to certain aspects of the present invention there are provided polypeptides, nucleotide sequences, nucleic acids, vectors, methods and uses in accordance with the following points.

1. A modified FIX (factor IX) polypeptide comprising:
an amino acid chosen from the group consisting of: leucine, cysteine, aspartic acid, glutamic acid, histidine, lysine, asparagine, glutamine, tyrosine in a position corresponding to position 338.

2. A polypeptide according to claim 1 wherein the amino acid is chosen from the group consisting of: leucine, aspartic acid, glutamine.

3. A polypeptide according to claim 1 wherein the amino acid is chosen from the group consisting of: aspartic acid, glutamine.

4. A polypeptide according to claim 1 wherein the amino acid is aspartic acid.

5. A polypeptide according to claim 1 wherein the amino acid is glutamine.

6. A polypeptide according to claim 1 wherein the amino acid is leucine.

7. A polypeptide according to one of the previous points, and having a homology of at least 70% with a peptide sequence selected from the group consisting of: SEQ ID NO: 1 and SEQ ID NO: 2.

8. A polypeptide according to one of the previous points, and having a homology of at least 90% with a peptide sequence selected from the group consisting of: SEQ ID NO: 1 and SEQ ID NO: 2.

9. A polypeptide according to one of the previous points, and having a percentage identity of at least 70% with a peptide sequence selected from the group consisting of: SEQ ID NO: 1 and SEQ ID NO: 2.

10. A polypeptide according to one of the previous points, and having a percentage identity of at least 90% with a peptide sequence selected from the group consisting of: SEQ ID NO: 1 and SEQ ID NO: 2.

11. A polypeptide according to one of the previous points wherein the peptide sequence is SEQ ID NO: 2.

12. A nucleotide sequence encoding a FIX polypeptide according to one of the previous points.

13. A nucleotide sequence according to point 12 wherein the nucleotide sequence is a DNA sequence and consists of intron portions and exon portions, the exon portions having an overall sequence with at least 70% homology relative to an overall sequence of exon regions of a SEQ ID NO: 5 sequence.

14. A nucleotide sequence according to point 13 wherein the overall sequence of the exon portions has at least 90% homology with the overall sequence of the exon regions of the SEQ ID NO: 5 sequence.

15. A nucleotide sequence according to one of points 12 to 14 wherein the nucleotide sequence has at least 50% homology with the sequence having the accession number K02402 (GenBank).

16. A nucleotide sequence according to one of points 12 to 15, comprising in positions corresponding to 34098, 34099 and 34100 a triplet chosen from the group consisting of: TTA, UUA, TTG, UUG, CTT, CUU, CTC, CUC, CTA, CUA, CTG, CUG, GAT, GAU, GAC, CAA, CAG.

17. A nucleotide sequence according to point 16, comprising in positions corresponding to 34098, 34099 and 34100 a triplet chosen from the group consisting of: TTA, UUA, TTG, UUG, CTT, CUU, CTC, CUC, CTA, CUA, CTG, CUG, CAA, CAG.

18. A nucleotide sequence according to point 16, comprising in positions corresponding to 34098, 34099 and 34100 a triplet chosen from the group consisting of: TTA, UUA, TTG, UUG, CTT, CUU, CTC, CUC, CTA, CUA, CTG, CUG.

19. A nucleotide sequence according to point 16, comprising in positions corresponding to 34098, 34099 and 34100 a triplet chosen from the group consisting of: CAA, CAG.

20. A nucleotide sequence according to point 16, comprising in positions corresponding to 34098, 34099 and 34100 a triplet chosen from the group consisting of: GAT, GAU, GAC, CAA, CAG.

21. A nucleotide sequence according to point 16, comprising in positions corresponding to 34098, 34099 and 34100 a triplet chosen from the group consisting of: GAT, GAU, GAC.

22. A nucleotide sequence according to one of points 12 to 18, comprising a thymine in a position corresponding to position 34099.

23. A nucleic acid comprising a nucleotide sequence according to one of points 12 to 22.

24. A nucleic acid according to point 23, and comprising a promoter in operational linkage with said nucleotide sequence.

25. A vector comprising a nucleic acid according to point 23 or 24.

26. A method for producing a modified FIX polypeptide, whereby the modified FIX polypeptide is expressed by means of a nucleic acid according to point 23 or 24.

27. A method according to point 26, comprising the steps of:
introducing a vector of point 25 into a cell; and
culturing the cell such that the FIX polypeptide is expressed.

28. A modified FIX polypeptide according to one of points 1 to 11 for use as a medicament.

29. A modified FIX polypeptide according to one of points 1 to 11 for the treatment of at least one coagulopathy.

30. Use of a modified FIX polypeptide according to one of points 1 to 11 for preparing a drug for the treatment of at least one coagulopathy in a mammal.

31. A nucleotide sequence according to one of points 12 to 22 for use as a medicament.

32. A method for detecting the nucleotide sequence of one of points 12 to 22.

33. A method for detecting the modified FIX polypeptide according to one of points 1 to 11.

34 A method according to point 32 comprising an step of amplification by PCR.

BIBLIOGRAPHY

Ameri A, Kurachi S, Sueishi K, Kuwahara M, Kurachi K. Myocardial fibrosis in mice with overexpression of human blood coagulation factor IX. Blood. 2003 Mar. 1; 101 (5):1871-3. Epub 2002 Oct. 24.

Chang J L, Jin J P, Lollar P, et al. Changing residue 338 in human factor IX from arginine to alanine causes an increase in catalytic activity. J Biol Chem 1998; 273: 12089-12094.

Lowe G D O. Factor IX and thrombosis. British Journal of Haematology, 2001, 115, 507-513.

Kunkel T A. Rapid and efficient site-specific mutagenesis without phenotypic selection. Proc Natl Acad Sci USA 1985, 82:488-492.

Kurachi K, Davie E W. Isolation and characterization of a cDNA coding for human factor IX. Proc Natl Acad Sci USA 1982; 79:6461-6464.

Murphy S L, High K A. Gene therapy for haemophilia. Br J Haematol. 2008 March; 140(5):479-87.

Yoshitake S, Schach B G, Foster D C, et al. Nucleotide Sequence of thr Gene for Human Factor IX (Antihemophilic Factor B). Biochemistry 1985; 24:3736-3750.

Toomey J R, Valocik R E, Koster P F, Gabriel M A, McVey M, Hart T K, Ohlstein E H, Parsons A A, Barone F C. Inhibition of factor IX(a) is protective in a rat model of thromboembolic stroke. Stroke. 2002 February; 33(2): 578-85.

The invention claimed is:

1. A method of treating a coagulopathy in a human patient, comprising administering a vector to the human patient, wherein:
    a. the vector is an adeno-associated virus;
    b. the vector comprises a nucleic acid encoding a modified FIX polypeptide, the modified FIX polypeptide comprising at least 70% identity to SEQ ID NO: 2 and a leucine in position 338 of SEQ ID NO: 2; and
    c. the vector comprises promoter sequences and transcription termination and control elements;
    thereby treating the coagulopathy.

2. The method of claim 1, wherein the modified FIX polypeptide is expressed in the human patient at a level at least five fold less than the level of wild-type FIX of SEQ ID NO: 2 in a healthy human lacking the coagulopathy.

3. The method of claim 1, wherein the nucleic acid encodes a modified FIX polypeptide identical to SEQ ID NO: 2 except for the leucine at position 338.

4. The method of claim 1, wherein the nucleic acid integrates stably into the human patient's genome.

5. The method of claim 1, wherein the adeno-associated virus vector is administered at a dose of 1 to $10^{14}$ particles per kilogram of patient weight.

6. The method of claim 1, wherein the adeno-associated virus vector is administered at a dose of $10^6$ to $10^{12}$ particles per kilogram of patient weight.

7. The method of claim 1, wherein the coagulopathy is a deficiency in FIX.

8. The method of claim 7, wherein the deficiency in FIX is a genetic deficiency in FIX.

9. The method of claim 7, wherein the coagulopathy is hemophilia B.

10. The method of claim 8, wherein the coagulopathy is hemophilia B.

11. The method of claim 2, wherein the healthy human expresses 5 µg/ml of wild-type FIX.

12. The method of claim 11, wherein the 5 µg/ml of wild-type FIX is measured in plasma from the healthy human.

13. The method of claim 1, wherein the modified FIX polypeptide is expressed at a daily dosage between 0.1 µg/kg and 400 µg/kg body weight.

14. The method of claim 1, wherein the modified FIX polypeptide is expressed at a level that does not cause thrombotic complications.

15. The method of claim 1, wherein the modified FIX polypeptide is expressed at a level that does not lead to neutralizing antibody generation.

16. The method of claim 1, wherein the modified FIX polypeptide is expressed at a level that reduces and/or prevents hemorrhages.

17. The method of claim 2, wherein the modified FIX polypeptide is expressed in the human patient at a level of seven to nine fold less than the level of wild-type FIX of SEQ ID NO: 2 in the healthy human.

18. The method of claim 2, wherein the modified FIX polypeptide is expressed in the human patient at a level of eight to nine fold less than the level of wild-type FIX of SEQ ID NO: 2 in the healthy human.

19. The method of claim 1, wherein the nucleic acid encodes for a FIX polypeptide precursor comprising at least 70% identity to SEQ ID NO: 1, said FIX polypeptide precursor comprising the modified FIX polypeptide.

20. The method of claim 1, wherein the nucleic acid comprises an overall sequence having at least 70% homology with the overall sequence of exon regions in the sequence having accession number K02402 (GenBank).

* * * * *

(12) INTER PARTES REVIEW CERTIFICATE (4171st)

United States Patent
Simioni

(10) Number: US 9,982,248 K1
(45) Certificate Issued: Oct. 30, 2025

(54) FACTOR IX POLYPEPTIDE MUTANT, ITS USES AND METHOD FOR ITS PRODUCTION

(71) Applicant: Paolo Simioni

(72) Inventor: Paolo Simioni

(73) Assignee: UNIQURE BIOPHARMA B.V.

Trial Numbers:

IPR2021-00925 filed May 11, 2021
IPR2021-00926 filed May 11, 2021

Inter Partes Review Certificate for:

Patent No.: 9,982,248
Issued: May 29, 2018
Appl. No.: 15/650,070
Filed: Jul. 14, 2017

The results of IPR2021-00925 and IPR2021-00926 are reflected in this inter partes review certificate under 35 U.S.C. 318(b).

INTER PARTES REVIEW CERTIFICATE
U.S. Patent 9,982,248 K1
Trial No. IPR2021-00925
Certificate Issued Oct. 30, 2025

AS A RESULT OF THE INTER PARTES REVIEW PROCEEDING, IT HAS BEEN DETERMINED THAT:

Claims 1-20 are cancelled.

\* \* \* \* \*

SEQUENCE LISTING

```
<160> NUMBER OF SEQ ID NOS: 13

<210> SEQ ID NO 1
<211> LENGTH: 461
<212> TYPE: PRT
<213> ORGANISM: Homo sapiens
<220> FEATURE:
<221> NAME/KEY: SIGNAL
<222> LOCATION: 1..56
<223> OTHER INFORMATION: SIGNAL PEPTIDE
<220> FEATURE:
<221> NAME/KEY: PEPTIDE
<222> LOCATION: 1..461
<220> FEATURE:
<221> NAME/KEY: SITE
<222> LOCATION: 384..384
<223> OTHER INFORMATION: Arg RESIDUE CORRESPONDING TO 338 OF SEQ ID
      No. 2
<220> FEATURE:
<221> NAME/KEY: SITE
<222> LOCATION: 384..384
<223> OTHER INFORMATION: RESIDUE MUTATED IN THE CLAIMED INVENTION
<300> PUBLICATION INFORMATION:
<308> DATABASE ACCESSION NUMBER: GenBANK AAB59620.1
<309> DATABASE ENTRY DATE: 1996-04-30
<313> RELEVANT RESIDUES IN SEQ ID NO: (1)..(461)

<400> SEQUENCE: 1

Met Gln Arg Val Asn Met Ile Met Ala Glu Ser Pro Gly Leu Ile Thr
1               5                   10                  15
```

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

```
Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
450                 455                 460

<210> SEQ ID NO 2
<211> LENGTH: 415
<212> TYPE: PRT
<213> ORGANISM: Homo sapiens
<220> FEATURE:
<221> NAME/KEY: PEPTIDE
<222> LOCATION: 1..415
<220> FEATURE:
<221> NAME/KEY: SITE
<222> LOCATION: 338..338
<223> OTHER INFORMATION: RESIDUE CORRESPONDING TO 384 OF SEQ ID No. 2
<220> FEATURE:
<221> NAME/KEY: SITE
<222> LOCATION: 338..338
<223> OTHER INFORMATION: RESIDUE MUTATED IN THE CLAIMED INVENTION
<300> PUBLICATION INFORMATION:
<308> DATABASE ACCESSION NUMBER: NCBI/NP_000124
<309> DATABASE ENTRY DATE: 2009-07-12
<313> RELEVANT RESIDUES IN SEQ ID NO: (1)..(415)

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270
```

```
Leu Glu Leu Asp Glu Pro Leu Val Leu Asn Ser Tyr Val Thr Pro Ile
        275                 280                 285
Cys Ile Ala Asp Lys Glu Tyr Thr Asn Ile Phe Leu Lys Phe Gly Ser
        290                 295                 300
Gly Tyr Val Ser Gly Trp Gly Arg Val Phe His Lys Gly Arg Ser Ala
305                 310                 315                 320
Leu Val Leu Gln Tyr Leu Arg Val Pro Leu Val Asp Arg Ala Thr Cys
                325                 330                 335
Leu Arg Ser Thr Lys Phe Thr Ile Tyr Asn Asn Met Phe Cys Ala Gly
            340                 345                 350
Phe His Glu Gly Gly Arg Asp Ser Cys Gln Gly Asp Ser Gly Gly Pro
        355                 360                 365
His Val Thr Glu Val Glu Gly Thr Ser Phe Leu Thr Gly Ile Ile Ser
        370                 375                 380
Trp Gly Glu Glu Cys Ala Met Lys Gly Lys Tyr Gly Ile Tyr Thr Lys
385                 390                 395                 400
Val Ser Arg Tyr Val Asn Trp Ile Lys Glu Lys Thr Lys Leu Thr
                405                 410                 415
```

<210> SEQ ID NO 3
<211> LENGTH: 1381
<212> TYPE: RNA
<213> ORGANISM: Homo sapiens

<400> SEQUENCE: 3

| | | | | |
|---|---|---|---|---|
| ugcagcgcgu | gaacaugauc | auggcagaau | caccaggccu | caucaccauc | ugccuuuuag | 60 |
| gauaucuacu | cagugcugaa | uguacaguuu | ucuugauca | ugaaaacgcc | aacaaaauuc | 120 |
| ugaaucggcc | aaagagguau | aauucaggua | aauuggaaga | guugguucaa | gggaaccuug | 180 |
| agagagaaug | uauggaagaa | aaguguaguu | uugaagaagc | acgagaaguu | uugaaaaca | 240 |
| cugaaagaac | aacugaauuu | uggaagcagu | auguugaugg | agaucagugu | gaguccaauc | 300 |
| caugauuuaaa | uggcggcagu | ugcaaggaug | acauuaauuc | cuaugaaugu | ugguguccu | 360 |
| uuggauuuga | aggaaagaac | ugugaauuag | auguaacaug | uaacauuaag | aauggcagau | 420 |
| gcgagcaguu | uuguaaaaau | agcugauaua | caagguggu | uugcuccugu | acugagggau | 480 |
| aucgacuugc | agaaaaccag | aaguccugug | aaccagcagu | gccauuucca | uguggaagag | 540 |
| uuucuguuuc | acaaacuucu | aagcucaccc | gugcugaggc | uguuuuccu | gauguggacu | 600 |
| auguaaauuc | uacugaagcu | gaaaccauuu | uggauaacau | cacucaaagc | acccaaucau | 660 |
| uuaaugacuu | cacucggguu | guugguggag | aagauguggcaa | accaggucaa | uucccuuggc | 720 |
| agguuguuuu | ugaauggaaaa | guugaugcau | ucuguggaagg | cucuaucguu | aaugaaaaau | 780 |
| ggauuguaac | ugcugcccac | ugauguugaaaa | cugguguuaa | aauuacaguu | gucgcaggug | 840 |
| aacauaauau | ugaggagaca | gaacauacag | agcaaaagcg | aaaugugauu | cgaauuauuc | 900 |
| cucaccacaa | cuacaaugca | gcuauuaaua | aguacaacca | ugacauugcc | cuucuggaac | 960 |
| uggacgaacc | cuuagugcua | aacagcuacg | uuacaccuau | uugcauugcu | gacaaggaau | 1020 |
| acacgaaacau | cuuccucaaa | uuuggaucug | gcuauguaag | uggcuggga | agagucuucc | 1080 |
| acaaagggag | aucagcuuua | guucuucagu | accuuagagu | uccacuuguu | gaccgagcca | 1140 |
| caugucuucg | aucacaaag | uucaccaucu | auaacaacau | guucugugcu | ggcuuccaug | 1200 |
| aaggaggua | gagauucaugu | caaggagaua | guggggaggacc | ccauguuacu | gaaguggaag | 1260 |
| ggaccaguuu | cuuaacugga | auuauuagcu | ggggugaaga | gugugcaaug | aaaggcaaau | 1320 |

```
auggaauaua uaccaagguu ucccgguaug ucaacuggau uaaggaaaaa acaaagcuca    1380
c                                                                  1381

<210> SEQ ID NO 4
<211> LENGTH: 1243
<212> TYPE: RNA
<213> ORGANISM: Homo sapiens

<400> SEQUENCE: 4
auaauucagg uaaauuggaa gaguuuguuc aagggaaccu ugagagagaa uguauggaag      60
aaaaguguag uuuugaagaa gcacgagaag uuuuugaaaa cacugaaaga acaacugaau     120
uuuggaagca guauguugau ggagaucagu gugaguccaa uccauguuua aauggcggca     180
guugcaagga ugacauuaau uccuaugaau guuggugucc cuuuggauuu gaaggaaaga     240
acugugaauu agauguaaca uguaacauua agaauggcag augcgagcag uuuuguaaaa     300
auagugcuga uaacaaggug guuugcuccu guacugaggg auaucgacuu gcagaaaacc     360
agaaguccug ugaaccagca gugccauuuc cauguggaag aguuucuguu ucacaaacuu     420
cuaagcucac ccgugcugag gcuguuuuuc cugaugugga cuauguaaau ucuacugaag     480
cugaaaccau uuuggauaac aucacucaaa gcacccaauc auuuaaugac uucacucggg     540
uuguuggugg agaagaugcc aaaccagguc aauucccuug gcagguuguu ugaauggua      600 aaguugaugc auucuguggu ggcucuaucg uuaaugaaaa auggauugua acugcugccc     660 acugguuga aacuggugu aaaauuacag ugucgcagg ugaacauaau auugaggaga       720
cagaacauac agagcaaaag cgaaaugga uucgaauuau uccucaccac aacuacaaug      780
cagcuauuaa uaaguacaac caugacauug cccuucugga acuggacgaa cccuuagugc     840
uaaacagcua cguuacaccu auuugcauug cugacaagga auacacgaac aucuuccuca     900 aauuggauc uggcuaugua aguggcuggg gaagagucuu ccacaaaggg agaucagcuu      960
uaguucuuca guaccuuaga guuccacuug uugaccgagc cacaugucuu cgaucuacaa    1020
aguucaccau cuauaacaac auguucugug cuggcuucca ugaaggaggu agagauucau    1080
gucaaggaga uagugggggga ccccauguua cugaaguggga agggaccagu uucuuaacug    1140
gaauuauuag cuggggugaa gagugugcaa ugaaaggcaa auauggauua uauaccaagg    1200
uaucccggua ugucaacugg auuaaggaaa aacaaagcu cac                      1243

<210> SEQ ID NO 5
<211> LENGTH: 5280
<212> TYPE: DNA
<213> ORGANISM: Homo sapiens
<220> FEATURE:
<221> NAME/KEY: CDS
<222> LOCATION: 325..411
<223> OTHER INFORMATION: /transl_table=1
<220> FEATURE:
<221> NAME/KEY: misc_feature
<222> LOCATION: 600-601
<223> OTHER INFORMATION: /note="intron between positions 600-601 not
      shown, approx length 5400bp" /note="position 601 corresponds to
      position 6000 in Anson et al paper"
<220> FEATURE:
<221> NAME/KEY: CDS
<222> LOCATION: 776..940
<223> OTHER INFORMATION: /transl_table=1
<220> FEATURE:
<221> NAME/KEY: CDS
<222> LOCATION: 1129..1152
<223> OTHER INFORMATION: /transl_table=1
<220> FEATURE:
```

```
<221> NAME/KEY: misc_feature
<222> LOCATION: 1200-1201
<223> OTHER INFORMATION: /note="Intron between position 1200 and 1201,
      approx length 3960 bp" /note="position 1200 corresponds to
      position 6600 in Fig 4 of Anson et al paper, position 1201
      corresponds to position 10560 in Fig 4 of Anson et al."
<220> FEATURE:
<221> NAME/KEY: CDS
<222> LOCATION: 1264..1377
<223> OTHER INFORMATION: /transl_table=1
<220> FEATURE:
<221> NAME/KEY: misc_feature
<222> LOCATION: 1440-1441
<223> OTHER INFORMATION: /note="Intron present between positions 1440
      and 1441, approx length 7320 bp" /note="position 1440 corresponds
      to 10800 in Fig 4 of Anson et al, position 1441 corresponds to
      18120 in Fig 4 of Anson et al"
<220> FEATURE:
<221> NAME/KEY: CDS
<222> LOCATION: 1582..1710
<223> OTHER INFORMATION: /transl_table=1
<220> FEATURE:
<221> NAME/KEY: misc_feature
<222> LOCATION: 1800..1801
<223> OTHER INFORMATION: /note="Intron between positions 1880-1801,
      approx length 2400 bp" /note="position 1800 corresponds to
      position 18480 in Fig 4 of Anson et al, position 1801 corresponds
      to position 20880 of Anson et al"
<220> FEATURE:
<221> NAME/KEY: CDS
<222> LOCATION: 1881..2084
<223> OTHER INFORMATION: /transl_table=1
<220> FEATURE:
<221> NAME/KEY: misc_feature
<222> LOCATION: 2160..2161
<223> OTHER INFORMATION: /note="Intron between 2160 and 2161, approx
      length 9960 bp" /note="position 2160 corresponds to 21240 in Fig 4
      of Anson et al, position 2161 correspnds to 31080 of Fig 4 of
      Anson et al"
<220> FEATURE:
<221> NAME/KEY: CDS
<222> LOCATION: 2303..2416
<223> OTHER INFORMATION: /transl_table=1
<220> FEATURE:
<221> NAME/KEY: CDS
<222> LOCATION: 3085..3630
<223> OTHER INFORMATION: /transl_table=1
<220> FEATURE:
<221> NAME/KEY: misc_feature
<222> LOCATION: 3398
<223> OTHER INFORMATION: /note="equivalent to position 32318 in Figure
      4 of Anson et al paper"

<400> SEQUENCE: 5
ctctctgaca aagatacggt gggtcccact gatgaactgt gctgccacag taaatgtagc      60
cactatgcct atctccattc tgaagatgtg tcacttcctg tttcagactc aaatcagcca     120
cagtggcaga agcccacaga atcagaggtg aaatttaata atgaccactg cccattctct     180
tcacttgtcc caagaggcca ttggaaatag tccaaagacc cattgaggga gatggacatt     240
atttcccaga agtaaatacta gctcagcttg tactttggta caactaatcg accttaccac     300
tttcacaact tgctagcaga ggtt atg cag cgc gtg aac atg atc atg gca        351
                         Met Gln Arg Val Asn Met Ile Met Ala
                         1               5 gaa tca cca ggc ctc atc acc atc tgc ctt tta gga tat cta ctc agt       399
Glu Ser Pro Gly Leu Ile Thr Ile Cys Leu Leu Gly Tyr Leu Leu Ser
10              15              20              25 gct gaa tgt aca ggtttgtttc cttttttaaa atacattgag tatgcttgcc           451
Ala Glu Cys Thr ttttagatat agaaatatct gatgctgtct tcttcactaa attttgatta catgatttga     511
cagcaatatt gaagagtcta acagccagca cgcaggttgg taagtactgg ttctttgtta     571
```

```
gctaggtttt cttcttcttc attttttaaaa atctccatgt gtatacagta ctgtgggaac      631
atcacagatt ttggctccta tgccctaaag agaaattggc tttcagatta tttggattaa      691
aaacaaagac tttcttaaga gatgtaaaat tttcatgatg tttttctttt tgctaaaact      751
aaagaattat tcttttacat ttca gtt ttt ctt gat cat gaa aac gcc aac          802
                           Val Phe Leu Asp His Glu Asn Ala Asn
                            30              35 aaa att ctg aat cgg cca aag agg tat aat tca ggt aaa ttg gaa gag         850
Lys Ile Leu Asn Arg Pro Lys Arg Tyr Asn Ser Gly Lys Leu Glu Glu
     40              45              50 ttt gtt caa ggg aac ctt gag aga gaa tgt atg gaa gaa aag tgt agt         898
Phe Val Gln Gly Asn Leu Glu Arg Glu Cys Met Glu Glu Lys Cys Ser
 55              60              65              70 ttt gaa gaa gca cga gaa gtt ttt gaa aac act gaa aga aca                 940
Phe Glu Glu Ala Arg Glu Val Phe Glu Asn Thr Glu Arg Thr
             75              80 gtgagtattt ccacataata cccttcagat gcagagcata aatagaaaaa tctttaaaaa      1000
gacacttctc tttaaaattt taaagcatcc atatatattt atgtatgtta aatgttataa      1060
aagataggaa atcaatacca aaacacttta gatattaccg ttaatttgtc ttcttttatt      1120 ctttatag act gaa ttt tgg aag cag tat gtt ggtaagcaat tcattttatc         1172
        Thr Glu Phe Trp Lys Gln Tyr Val
             85              90 ctctagctaa tatatgaaac atatgagaca ggggaggacc gggcattcta agcagtttac      1232
gtgccaattc aatttcttaa cctatctcaa a gat gga gat cag tgt gag tcc         1284
                                   Asp Gly Asp Gln Cys Glu Ser
                                                    95 aat cca tgt tta aat ggc ggc agt tgc aag gat gac att aat tcc tat        1332
Asn Pro Cys Leu Asn Gly Gly Ser Cys Lys Asp Asp Ile Asn Ser Tyr
100             105             110             115 gaa tgt tgg tgt ccc ttt gga ttt gaa gga aag aac tgt gaa tta            1377
Glu Cys Trp Cys Pro Phe Gly Phe Glu Gly Lys Asn Cys Glu Leu
             120             125             130 ggtaagtaac tattttttga atactcatgg ttcaaagttt ccctctgaaa caagttgaaa      1437
ctgaaaattt ctctccccaa cgtatattgg gggcaacatg aatgccccca atgtatattt      1497
gacccataca tgagtcagta gttccatgta cttttttagaa atgcatgtta aatgatgctg     1557
ttactgtcta ttttgcttct ttta gat gta aca tgt aac att aag aat ggc         1608
                            Asp Val Thr Cys Asn Ile Lys Asn Gly
                                            135 aga tgc gag cag ttt tgt aaa aat agt gct gat aac aag gtg gtt tgc        1656
Arg Cys Glu Gln Phe Cys Lys Asn Ser Ala Asp Asn Lys Val Val Cys
140             145             150             155 tcc tgt act gag gga tat cga ctt gca gaa aac cag aag tcc tgt gaa        1704
Ser Cys Thr Glu Gly Tyr Arg Leu Ala Glu Asn Gln Lys Ser Cys Glu
             160             165             170 cca gca ggtcataatc tgaataagat ttttaaaga aatctgtat ctgaaacttc           1760
Pro Ala agcattttaa caaacctaca taatttttaat tcctacttga cctcaatctc aattttttgta    1820 atacatgttc catttgccaa tgagaaatat caggttacta attttctttc tattttttcta    1880 gtg cca ttt cca tgt gga aga gtt tct gtt tca caa act tct aag ctc        1928
Val Pro Phe Pro Cys Gly Arg Val Ser Val Ser Gln Thr Ser Lys Leu
     175             180             185 acc cgt gct gag gct gtt ttt cct gat gtg gac tat gta aat tct act        1976
Thr Arg Ala Glu Ala Val Phe Pro Asp Val Asp Tyr Val Asn Ser Thr
190             195             200             205
```

-continued

```
gaa gct gaa acc att ttg gat aac atc act caa agc acc caa tca ttt    2024
Glu Ala Glu Thr Ile Leu Asp Asn Ile Thr Gln Ser Thr Gln Ser Phe
            210                 215                 220 aat gac ttc act cgg gtt gtt ggt gga gaa gat gcc aaa cca ggt caa    2072
Asn Asp Phe Thr Arg Val Val Gly Gly Glu Asp Ala Lys Pro Gly Gln
        225                 230                 235 ttc cct tgg cag gtactttata ctgatggtgt gtcaaaactg gagctcagct        2124
Phe Pro Trp Gln
        240 ggcaagacac aggccaggtg ggagactgag gctattaaag ctcacatttc cagaaacatt  2184
ccatttctgc cagcacctag aagccaatat tttgcctatt cctgtaacca gcacacatat  2244
ttattttttt ctagatcaaa tgtattatgc agtaagagtc ttaattttgt tttcacag    2302 gtt gtt ttg aat ggt aaa gtt gat gca ttc tgt gga ggc tct atc gtt    2350
Val Val Leu Asn Gly Lys Val Asp Ala Phe Cys Gly Gly Ser Ile Val
                245                 250                 255 aat gaa aaa tgg att gta act gct gcc cac tgt gtt gaa act ggt gtt    2398
Asn Glu Lys Trp Ile Val Thr Ala Ala His Cys Val Glu Thr Gly Val
            260                 265                 270 aaa att aca gtt gtc gca ggtaaataca cagaaagaat aataatctgc           2446
Lys Ile Thr Val Val Ala
        275 agcaccacta gctctttaat atgattggta caccatattt tactaaggtc taataaaatt  2506
gttgttgaat aaattgggct aaaggcagaa gggtcataat ttcagaaccc acgtcgcacc  2566
gtcctccaag catccatagt tcttttgata taccccatt atcactcatt tcagtgaggt  2626
acaattagtt cttgatgtag ccatttccat accagaaggc cttcccaaaa atcagtgtca  2686
tgtcaccgat cctttatct ctggtgcttg gcacaacctg tagcaggtcc tcagaaaaca   2746
aacatttgaa ttaatggcca aatgagtttg tgctcaaaaa aggggtgagg atacttgaaa  2806
tttggaaaat ctaggataat tcatgactag tggattcatt atcaccaatg aaaggcttat  2866
aacagcatga gtgaacagaa ccatctctat gatagtcctg aatggctttt tggtctgaaa  2926
aatatgcatt ggctctcatt acatttaacc aaaattatca caatataaga atgagatctt  2986
taacattgcc aattaggtca gtggtcccaa gtagtcactt agaaaatctg tgtatgtgaa  3046
atactgtttg tgacttaaaa tgaaattat ttttaata ggt gaa cat aat att gag   3102
                                          Gly Glu His Asn Ile Glu
                                                  280         285 gag aca gaa cat aca gag caa aag cga aat gtg att cga att att cct    3150
Glu Thr Glu His Thr Glu Gln Lys Arg Asn Val Ile Arg Ile Ile Pro
            290                 295                 300 cac cac aac tac aat gca gct att aat aag tac aac cat gac att gcc    3198
His His Asn Tyr Asn Ala Ala Ile Asn Lys Tyr Asn His Asp Ile Ala
        305                 310                 315 ctt ctg gaa ctg gac gaa ccc tta gtg cta aac agc tac gtt aca cct    3246
Leu Leu Glu Leu Asp Glu Pro Leu Val Leu Asn Ser Tyr Val Thr Pro
    320                 325                 330 att tgc att gct gac aag gaa tac acg aac atc ttc ctc aaa ttt gga    3294
Ile Cys Ile Ala Asp Lys Glu Tyr Thr Asn Ile Phe Leu Lys Phe Gly
            335                 340                 345 tct ggc tat gta agt ggc tgg gga aga gtc ttc cac aaa ggg aga tca    3342
Ser Gly Tyr Val Ser Gly Trp Gly Arg Val Phe His Lys Gly Arg Ser
350                 355                 360                 365 gct tta gtt ctt cag tac ctt aga gtt cca ctt gtt gac cga gcc aca    3390
Ala Leu Val Leu Gln Tyr Leu Arg Val Pro Leu Val Asp Arg Ala Thr
            370                 375                 380
```

| | | |
|---|---|---|
| tgt ctt cga tct aca aag ttc acc atc tat aac aac atg ttc tgt gct<br>Cys Leu Arg Ser Thr Lys Phe Thr Ile Tyr Asn Asn Met Phe Cys Ala<br>385 390 395 | | 3438 |
| ggc ttc cat gaa gga ggt aga gat tca tgt caa gga gat agt ggg gga<br>Gly Phe His Glu Gly Gly Arg Asp Ser Cys Gln Gly Asp Ser Gly Gly<br>400 405 410 | | 3486 |
| ccc cat gtt act gaa gtg gaa ggg acc agt ttc tta act gga att att<br>Pro His Val Thr Glu Val Glu Gly Thr Ser Phe Leu Thr Gly Ile Ile<br>415 420 425 | | 3534 |
| agc tgg ggt gaa gag tgt gca atg aaa ggc aaa tat gga ata tat acc<br>Ser Trp Gly Glu Glu Cys Ala Met Lys Gly Lys Tyr Gly Ile Tyr Thr<br>430 435 440 445 | | 3582 |
| aag gta tcc cgg tat gtc aac tgg att aag gaa aaa aca aag ctc act<br>Lys Val Ser Arg Tyr Val Asn Trp Ile Lys Glu Lys Thr Lys Leu Thr<br>450 455 460 | | 3630 |
| taatgaaaga tggatttcca aggttaattc attggaattg aaaattaaca gggcctctca | | 3690 |
| ctaactaatc actttcccat cttttgttag atttgaatat atacattcta tgatcattgc | | 3750 |
| tttttctctt tacaggggag aatttcatat tttacctgag caaattgatt agaaaatgga | | 3810 |
| accactagag gaatataatg tgttaggaaa ttacagtcat ttctaagggc ccagcccttg | | 3870 |
| acaaaattgt gaagttaaat tctccactct gtccatcaga tactatggtt ctccactatg | | 3930 |
| gcaactaact cactcaattt tccctcctta gcagcattcc atcttcccga tcttctttgc | | 3990 |
| ttctccaacc aaaacatcaa tgtttattag ttctgtatac agtacaggat ctttggtcta | | 4050 |
| ctctatcaca aggccagtac cacactcatg aagaagaac acaggagtag ctgagaggct | | 4110 |
| aaaactcatc aaaaacacta ctccttttcc tctaccctat tcctcaatct tttacctttt | | 4170 |
| ccaaatccca atccccaaat cagttttttct ctttcttact ccctctctcc cttttaccct | | 4230 |
| ccatggtcgt taaggagag atgggggagca tcattctgtt atacttctgt acacagttat | | 4290 |
| acatgtctat caaacccaga cttgcttcca tagtggggac ttgcttttca gaacataggg | | 4350 |
| atgaagtaag gtgcctgaaa agtttggggg aaaagtttct ttcagagagt taagttattt | | 4410 |
| tatatatata atatatatat aaaatatata atatacaata taaatatata gtgtgtgtgt | | 4470 |
| gtatgcgtgt gtgtagacac acacgcatac acacatataa tggaagcaat aagccattct | | 4530 |
| aagagcttgt atggttatgg aggtctgact aggcatgatt tgacgaaggc aagattggca | | 4590 |
| tatcattgta actaaaaaag ctgacattga cccagacata ttgtactctt tctaaaaata | | 4650 |
| ataataataa tgctaacaga aagaagagaa ccgttcgttt gcaatctaca gctagtagag | | 4710 |
| actttgagga agaattcaac agtgtgtctt cagcagtgtt cagagccaag caagaagttg | | 4770 |
| aagttgccta gaccagagga cataagtatc atgtctcctt taactagcat accccgaagt | | 4830 |
| ggagaagggt gcagcaggct caaaggcata agtcattcca atcagccaac taagttgtcc | | 4890 |
| ttttctggtt tcgtgttcac catggaacat tttgattata gttaatcctt ctatcttgaa | | 4950 |
| tcttctagag agttgctgac caactgacgt atgtttccct ttgtgaatta ataaactggt | | 5010 |
| gttctggttc ataccttggc ttttttgtgga ttccattgat gtgaatcagt cacccctgtat | | 5070 |
| ttgatgatgc atgggactac tgacaaaatc actctgactc tgaccctgcc aagctgctgc | | 5130 |
| cttctccctgc cccaacctca cccccagcca ggcctcactc tttgctagtt cctttagtct | | 5190 |
| tttagtcaat atattttgt cttcgcatat aagtataaat aaacatattt ttaaatttct | | 5250 |
| ggctgggccc agtggctcac gcctataatc | | 5280 |

```
<210> SEQ ID NO 6
<211> LENGTH: 8
```

```
<212> TYPE: PRT
<213> ORGANISM: Homo sapiens
<220> FEATURE:
<223> OTHER INFORMATION: [CDS]:1129..1152 from SEQ ID NO 5

<400> SEQUENCE: 6

Thr Glu Phe Trp Lys Gln Tyr Val
1               5

<210> SEQ ID NO 7
<211> LENGTH: 29
<212> TYPE: PRT
<213> ORGANISM: Homo sapiens
<220> FEATURE:
<223> OTHER INFORMATION: [CDS]:325..411 from SEQ ID NO 5

<400> SEQUENCE: 7

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr
            20                  25

<210> SEQ ID NO 8
<211> LENGTH: 38
<212> TYPE: PRT
<213> ORGANISM: Homo sapiens
<220> FEATURE:
<223> OTHER INFORMATION: [CDS]:1264..1377 from SEQ ID NO 5

<400> SEQUENCE: 8

Asp Gly Asp Gln Cys Glu Ser Asn Pro Cys Leu Asn Gly Gly Ser Cys
1               5                   10                  15

Lys Asp Asp Ile Asn Ser Tyr Glu Cys Trp Cys Pro Phe Gly Phe Glu
            20                  25                  30

Gly Lys Asn Cys Glu Leu
            35

<210> SEQ ID NO 9
<211> LENGTH: 43
<212> TYPE: PRT
<213> ORGANISM: Homo sapiens
<220> FEATURE:
<223> OTHER INFORMATION: [CDS]:1582..1710 from SEQ ID NO 5

<400> SEQUENCE: 9

Asp Val Thr Cys Asn Ile Lys Asn Gly Arg Cys Glu Gln Phe Cys Lys
1               5                   10                  15

Asn Ser Ala Asp Asn Lys Val Val Cys Ser Cys Thr Glu Gly Tyr Arg
            20                  25                  30

Leu Ala Glu Asn Gln Lys Ser Cys Glu Pro Ala
            35                  40

<210> SEQ ID NO 10
<211> LENGTH: 55
<212> TYPE: PRT
<213> ORGANISM: Homo sapiens
<220> FEATURE:
<223> OTHER INFORMATION: [CDS]:776..940 from SEQ ID NO 5

<400> SEQUENCE: 10

Val Phe Leu Asp His Glu Asn Ala Asn Lys Ile Leu Asn Arg Pro Lys
1               5                   10                  15

Arg Tyr Asn Ser Gly Lys Leu Glu Glu Phe Val Gln Gly Asn Leu Glu
            20                  25                  30
```

```
Arg Glu Cys Met Glu Glu Lys Cys Ser Phe Glu Glu Ala Arg Glu Val
            35                  40                  45

Phe Glu Asn Thr Glu Arg Thr
        50                  55

<210> SEQ ID NO 11
<211> LENGTH: 68
<212> TYPE: PRT
<213> ORGANISM: Homo sapiens
<220> FEATURE:
<223> OTHER INFORMATION: [CDS]:1881..2084 from SEQ ID NO 5

<400> SEQUENCE: 11

Val Pro Phe Pro Cys Gly Arg Val Ser Val Ser Gln Thr Ser Lys Leu
1               5                   10                  15

Thr Arg Ala Glu Ala Val Phe Pro Asp Val Asp Tyr Val Asn Ser Thr
            20                  25                  30

Glu Ala Glu Thr Ile Leu Asp Asn Ile Thr Gln Ser Thr Gln Ser Phe
        35                  40                  45

Asn Asp Phe Thr Arg Val Val Gly Gly Glu Asp Ala Lys Pro Gly Gln
    50                  55                  60

Phe Pro Trp Gln
65

<210> SEQ ID NO 12
<211> LENGTH: 38
<212> TYPE: PRT
<213> ORGANISM: Homo sapiens
<220> FEATURE:
<223> OTHER INFORMATION: [CDS]:2303..2416 from SEQ ID NO 5

<400> SEQUENCE: 12

Val Val Leu Asn Gly Lys Val Asp Ala Phe Cys Gly Gly Ser Ile Val
1               5                   10                  15

Asn Glu Lys Trp Ile Val Thr Ala Ala His Cys Val Glu Thr Gly Val
            20                  25                  30

Lys Ile Thr Val Val Ala
        35

<210> SEQ ID NO 13
<211> LENGTH: 182
<212> TYPE: PRT
<213> ORGANISM: Homo sapiens
<220> FEATURE:
<223> OTHER INFORMATION: [CDS]:3085..3630 from SEQ ID NO 5

<400> SEQUENCE: 13

Gly Glu His Asn Ile Glu Glu Thr Glu His Thr Glu Gln Lys Arg Asn
1               5                   10                  15

Val Ile Arg Ile Ile Pro His His Asn Tyr Asn Ala Ala Ile Asn Lys
            20                  25                  30

Tyr Asn His Asp Ile Ala Leu Leu Glu Leu Asp Glu Pro Leu Val Leu
        35                  40                  45

Asn Ser Tyr Val Thr Pro Ile Cys Ile Ala Asp Lys Glu Tyr Thr Asn
    50                  55                  60

Ile Phe Leu Lys Phe Gly Ser Gly Tyr Val Ser Gly Trp Gly Arg Val
65                  70                  75                  80

Phe His Lys Gly Arg Ser Ala Leu Val Leu Gln Tyr Leu Arg Val Pro
                85                  90                  95
```

-continued

```
Leu Val Asp Arg Ala Thr Cys Leu Arg Ser Thr Lys Phe Thr Ile Tyr
            100                 105                 110

Asn Asn Met Phe Cys Ala Gly Phe His Glu Gly Gly Arg Asp Ser Cys
        115                 120                 125

Gln Gly Asp Ser Gly Gly Pro His Val Thr Glu Val Glu Gly Thr Ser
    130                 135                 140

Phe Leu Thr Gly Ile Ile Ser Trp Gly Glu Glu Cys Ala Met Lys Gly
145                 150                 155                 160

Lys Tyr Gly Ile Tyr Thr Lys Val Ser Arg Tyr Val Asn Trp Ile Lys
                165                 170                 175

Glu Lys Thr Lys Leu Thr
            180
```